(12) United States Patent
Shyu et al.

(10) Patent No.: US 12,646,352 B2
(45) Date of Patent: Jun. 2, 2026

(54) ELECTRONIC DEVICE UNLOCKED AND CONTROLLED BY GESTURE RECOGNITION

(71) Applicant: PixArt Imaging Inc., Hsin-Chu County (TW)

(72) Inventors: Ning Shyu, Hsin-Chu County (TW); Shih-Feng Chen, Hsin-Chu County (TW); Han-Lin Chiang, Hsin-Chu County (TW); Yen-Min Chang, Hsin-Chu County (TW); Guo-Zhen Wang, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 346 days.

(21) Appl. No.: 18/196,250

(22) Filed: May 11, 2023

(65) Prior Publication Data

US 2023/0282023 A1 Sep. 7, 2023

Related U.S. Application Data

(60) Continuation-in-part of application No. 17/470,358, filed on Sep. 9, 2021, now Pat. No. 11,615,642, and
(Continued)

(30) Foreign Application Priority Data

Jun. 1, 2016 (TW) ................................. 105117190

(51) Int. Cl.
*G06K 9/00* (2022.01)
*A61B 5/00* (2006.01)
(Continued)

(52) U.S. Cl.
CPC .......... *G06V 40/161* (2022.01); *A61B 5/0008* (2013.01); *A61B 5/01* (2013.01);
(Continued)

(58) Field of Classification Search
None
See application file for complete search history.

(56) References Cited

U.S. PATENT DOCUMENTS

| | | | |
|---|---|---|---|
| 5,689,241 A | 11/1997 | Clarke, Sr. | |
| 6,529,617 B1 | 3/2003 | Prokoski | |

(Continued)

FOREIGN PATENT DOCUMENTS

| | | | |
|---|---|---|---|
| CN | 107084795 A | 8/2017 | |
| CN | 108416968 A | 8/2018 | |

(Continued)

OTHER PUBLICATIONS

JP-2019010927-A (machine translation) (Year: 2019).*
(Continued)

*Primary Examiner* — Feng Niu
(74) *Attorney, Agent, or Firm* — WPAT, PC

(57) ABSTRACT

There is provided an electronic device capable of improving the difficulty of breaking a digital electronic lock and the accuracy of gesture control. The electronic device is unlocked according to gestures of a single hand or two hands, an operation hand, a gesture position, a staying time of gesture and a gesture variation of a user. The electronic device further improves the accuracy of gesture control in conjunction with an accessory pattern, temperature sensing and space information of a wearable device. The present disclosure further provides an electronic device that identifies legitimacy of moving the electronic device according to a variation sequence of 3-axis accelerations of an accelerometer.

9 Claims, 19 Drawing Sheets

Related U.S. Application Data a continuation-in-part of application No. 17/334,600, filed on May 28, 2021, now Pat. No. 11,756,331, said application No. 17/470,358 is a division of application No. 16/442,783, filed on Jun. 17, 2019, now Pat. No. 11,328,152, said application No. 17/334,600 is a continuation of application No. 15/371,909, filed on Dec. 7, 2016, now abandoned.

(51) Int. Cl.

| | |
|---|---|
| *A61B 5/01* | (2006.01) |
| *A61B 5/11* | (2006.01) |
| *A61B 5/1171* | (2016.01) |
| *G01J 5/00* | (2022.01) |
| *G01J 5/02* | (2022.01) |
| *G06F 18/22* | (2023.01) |
| *G06F 18/25* | (2023.01) |
| *G06F 21/32* | (2013.01) |
| *G06V 10/143* | (2022.01) |
| *G06V 10/74* | (2022.01) |
| *G06V 10/80* | (2022.01) |
| *G06V 40/10* | (2022.01) |
| *G06V 40/16* | (2022.01) |
| *G06V 40/20* | (2022.01) |
| *G06V 40/40* | (2022.01) |

(52) U.S. Cl.
CPC ............ *A61B 5/015* (2013.01); *A61B 5/1114* (2013.01); *A61B 5/1176* (2013.01); *A61B 5/681* (2013.01); *A61B 5/6898* (2013.01); *A61B 5/742* (2013.01); *A61B 5/746* (2013.01); *G01J 5/0025* (2013.01); *G01J 5/026* (2013.01); *G06F 18/22* (2023.01); *G06F 18/251* (2023.01); *G06F 21/32* (2013.01); *G06V 10/143* (2022.01); *G06V 10/761* (2022.01); *G06V 10/803* (2022.01); *G06V 40/113* (2022.01); *G06V 40/168* (2022.01); *G06V 40/172* (2022.01); *G06V 40/20* (2022.01); *G06V 40/28* (2022.01); *G06V 40/45* (2022.01); *A61B 5/1123* (2013.01); *A61B 5/1171* (2016.02); *A61B 5/4839* (2013.01); *A61B 5/6893* (2013.01); *A61B 2560/0242* (2013.01); *A61B 2560/0252* (2013.01); *G01J 2005/0077* (2013.01); *G06V 40/117* (2022.01); *G06V 40/16* (2022.01)

(56) References Cited

U.S. PATENT DOCUMENTS

| | | | | |
|---|---|---|---|---|
| 8,233,047 | B2 | 7/2012 | Shimbo et al. | |
| 8,558,759 | B1 * | 10/2013 | Prada Gomez | G06F 3/017 345/619 |
| 9,298,267 | B2 * | 3/2016 | Lim | G06V 10/255 |
| 9,529,513 | B2 * | 12/2016 | Balan | G06F 3/0304 |
| 9,603,566 | B2 | 3/2017 | Chen | |
| 9,928,413 | B2 * | 3/2018 | Baca | G06F 21/00 |
| 10,029,047 | B2 | 7/2018 | Gupta et al. | |
| 10,579,153 | B2 * | 3/2020 | Smith | G06F 3/167 |
| 10,606,364 | B2 * | 3/2020 | Smith | G06F 3/017 |
| 10,642,369 | B2 * | 5/2020 | Iyer | G06V 40/11 |
| 10,650,036 | B2 | 5/2020 | Kimura et al. | |
| 10,691,943 | B1 | 6/2020 | Ferstl et al. | |
| 10,936,051 | B2 * | 3/2021 | Iyer | G02B 27/017 |
| 10,970,373 | B2 * | 4/2021 | Lee | G06F 3/0488 |

| | | | | |
|---|---|---|---|---|
| 11,157,605 | B2 | 10/2021 | Guo et al. | |
| 11,328,152 | B2 | 5/2022 | Chen et al. | |
| 11,350,167 | B2 | 5/2022 | Lee | |
| 11,606,493 | B2 | 3/2023 | Mishra | |
| 11,615,642 | B2 | 3/2023 | Chen et al. | |
| 11,615,871 | B2 | 3/2023 | Gupta et al. | |
| 11,677,900 | B2 * | 6/2023 | Nakamura | H04N 23/60 348/77 |
| 11,789,527 | B1 | 10/2023 | Bilous | |
| 12,314,466 | B2 * | 5/2025 | Bilous | G06F 3/012 |
| 2010/0289912 | A1 * | 11/2010 | Katz | H04N 23/611 348/222.1 |
| 2013/0281883 | A1 | 10/2013 | Nishida | |
| 2013/0342691 | A1 | 12/2013 | Lewis et al. | |
| 2015/0040040 | A1 * | 2/2015 | Balan | G06F 3/011 715/762 |
| 2015/0323388 | A1 | 11/2015 | Kostic et al. | |
| 2015/0373307 | A1 | 12/2015 | Huang et al. | |
| 2016/0034747 | A1 | 2/2016 | Jo et al. | |
| 2016/0162039 | A1 * | 6/2016 | Eilat | G06F 3/005 382/103 |
| 2018/0075032 | A1 * | 3/2018 | Kimura | G06F 1/3287 |
| 2018/0189547 | A1 | 7/2018 | Daniels et al. | |
| 2019/0328312 | A1 * | 10/2019 | Schroeder | H04N 23/23 |
| 2019/0384405 | A1 * | 12/2019 | Iyer | G06V 40/113 |
| 2019/0384406 | A1 * | 12/2019 | Smith | G06V 40/113 |
| 2019/0384407 | A1 * | 12/2019 | Smith | G06V 40/11 |
| 2020/0019681 | A1 | 1/2020 | Shoenfeld | |
| 2020/0042683 | A1 * | 2/2020 | Lee | H04L 63/0861 |
| 2020/0097065 | A1 * | 3/2020 | Iyer | G06F 3/017 |
| 2020/0159368 | A1 | 5/2020 | Han et al. | |
| 2020/0160081 | A1 | 5/2020 | Nakamura | |
| 2020/0238952 | A1 | 7/2020 | Lindsay et al. | |
| 2021/0294482 | A1 * | 9/2021 | Ikeda | G06V 40/28 |
| 2021/0397817 | A1 | 12/2021 | Su et al. | |
| 2021/0401291 | A1 | 12/2021 | Schriek et al. | |
| 2022/0203996 | A1 * | 6/2022 | Katz | B60W 50/14 |
| 2023/0027040 | A1 * | 1/2023 | Wang | G06V 10/809 |
| 2024/0036639 | A1 | 2/2024 | Bilous | |

FOREIGN PATENT DOCUMENTS

| | | | | | |
|---|---|---|---|---|---|
| CN | 109377628 | A | | 2/2019 | |
| CN | 105956520 | B | | 10/2019 | |
| CN | 112101216 | A | * | 12/2020 | G06V 40/16 |
| CN | 112733632 | A | * | 4/2021 | G06N 3/045 |
| JP | 2015161476 | A | | 9/2015 | |
| JP | 2019010927 | A | * | 1/2019 | |
| WO | WO-2008066130 | A1 | | 6/2008 | |
| WO | WO-2020097830 | A1 | * | 5/2020 | G06F 3/01 |

OTHER PUBLICATIONS

CN-112733632-A (machine translation) (Year: 2021).*
WO-2020097830-A1 (machine translation) (Year: 2020).*
CN-112101216-A (Year: 2020).*
Miaou et al., "A customized human fall detection system using omni-camera images and personal information." In 1st Transdisciplinary Conference on Distributed Diagnosis and Home Healthcare, 2006. D2H2., pp. 39-42. IEEE, 2006.
Toreyin et al., "Falling person detection using multi-sensor signal processing." EURASIP Journal on Advances in Signal Processing 2008 (2007): 1-7, Hindawi Publishing Corporation.
Marrin et al., "A meta-analytic approach to quantify the dose-response relationship between melatonin and core temperature." European Journal of Applied Physiology 113 (2013): 2323-2329. (Year:2013).
Renevey et al., "Photoplethysmography-Based Bracelet for Automatic Sleep Stages Classification: Preliminary Results", Iasted 2014, Zurich,Switzerland (Year: 2014).

* cited by examiner

100 thermal sensor image sensor

Ih

Im processor memory

11

13

14

12

FOV2

FOV1

11

12

200

600

61 — thermal sensor

Ih

62 — image sensor

Im

65 — gesture sensor

Sg

66 — wireless device

Swls

63 processor

64 memory

S_3ax 3-axis accelerometer — 67

Depth

121

ELECTRONIC DEVICE UNLOCKED AND CONTROLLED BY GESTURE RECOGNITION

CROSS REFERENCE TO RELATED APPLICATION

The present application is a continuation-in-part application of U.S. application Ser. No. 17/470,358, filed on Sep. 9, 2021, which is a divisional application of U.S. application Ser. No. 16/442,783, filed on Jun. 17, 2019, the disclosures of which are hereby incorporated by reference herein in their entirety.

The present application is also a continuation-in-part application of U.S. application Ser. No. 17/334,600, filed on May 28, 2021, which is a continuation application of U.S. application Ser. No. 15/371,909, filed on Dec. 7, 2016, and claims the priority benefit of Taiwan Patent Application Serial Number 105117190, filed on Jun. 1, 2016 the disclosures of which are hereby incorporated by reference herein in their entirety.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

BACKGROUND

1. Field of the Disclosure

This disclosure generally relates to the unlocking and the gesture control of an electronic device and, more particularly, to an electronic device that is unlocked without using physiological characteristics and performs the gesture control in conjunction with temperature sensing and a wearable device.

2. Description of the Related Art

The image sensor has been broadly adapted to portable devices as an unlocking means. However, it is difficult to directly use an image sensor to identify a living body in some scenarios, and the image sensor further has a problem of being easily affected by ambient light. In order to solve these issues, a complicated algorithm generally has to be used.

For example, physiological characteristics can be used to unlock a digital electronic lock. However, in a system having many users, the physiological characteristics of all the users have to be registered previously, e.g., including fingerprints or facial features, and thus it is very troublesome.

In addition, although controlling an electronic device by gestures has been provided in the art, the gesture control can be easily influenced by environment, e.g., other humans or objects similar to a shape of human hand on the scene can degrade the recognition accuracy such that most users don't want to use the gesture control.

Accordingly, the present disclosure provides an electronic device that can decrease the risk of being broken even without using physiological characteristics and also can reduce the environmental interference.

SUMMARY

The present disclosure provides an electronic device that is unlocked according to gestures (including predetermined gestures and user-defined gestures) of a single hand or two hands, an operation hand (left hand or right hand), a gesture position (or hand position), a staying time of gesture and a gesture variation (e.g., dynamic gesture), and an unlocking method thereof.

The present disclosure further provides an electronic device that has improved control accuracy by operating in conjunction with an accessory pattern, temperature sensing and space information of a wearable device, and a gesture recognition method thereof.

The present disclosure further provides an electronic device that identifies legitimacy of moving the electronic device according to a variation sequence of three-axis accelerations of a three-axis accelerometer, and a movement alarm method thereof.

The present disclosure provides an electronic device including an image sensor, a gesture sensor and a processor. The image sensor is configured to output an image frame for detecting a human face image. The gesture sensor is configured to generate a gesture detection signal. The processor is configured to recognize whether a human face is covered or not according to the human face image, recognize a gesture combination according to the gesture detection signal upon the human face not being covered, and unlock the electronic device upon the gesture combination matching a predetermined condition.

The present disclosure further provides an electronic device including an image sensor and a processor. The image sensor is configured to acquire an image frame containing a hand image. The processor is configured to recognize a specific pattern in the image frame associated with an accessory, perform a gesture recognition according to the hand image and the specific pattern in the image frame, and control the electronic device to perform a corresponding control according to a recognized gesture.

The present disclosure provides an electronic device including a three-axis accelerometer and a processor. The three-axis accelerometer is configured to output acceleration values in three axes. The processor is configured to receive the acceleration values in three axes, identify whether a variation of the acceleration values in three axes matches a predetermined sequence, and turn off an alarm function upon the predetermined sequence being matched.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 1:
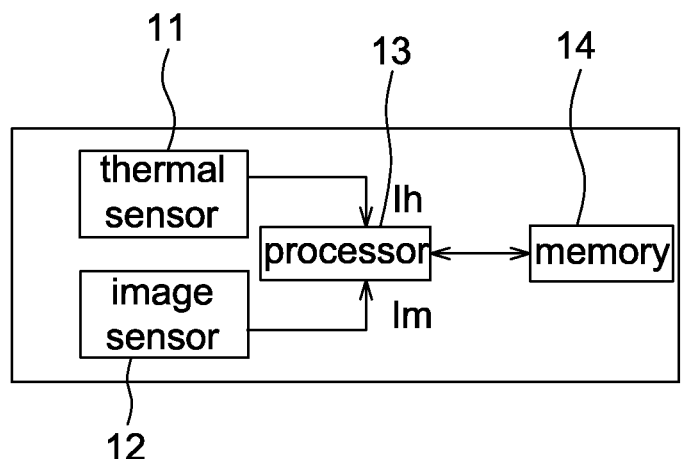
FIG. 1 is a block diagram of a recognition system according to one embodiment of the present disclosure.

Referring to FIG. 1, it is a schematic block diagram of a recognition system 100 according to one embodiment of the present disclosure. The recognition system 100 is applicable to a portable device including electronic devices such as a cell phone, a tablet computer, a notebook computer or the like; and the recognition system 100 is also applicable to a wearable device including electronic devices such as a watch, a bracelet, an armband or the like, but not limited thereto. The recognition system 100 includes a thermal sensor 11, an image sensor 12, a processor 13 and a memory 14. The recognition system 100 performs at least the face recognition and the gesture recognition.

The thermal sensor 11 includes a Pyroelectric Infrared (PIR) type, a thermopile type or a bolometer type sensor, which is used to detect infrared light and output electrical signals (e.g., voltage or current signals) or digital signals to respond to detected temperatures. Preferably, the thermal sensor 11 outputs a two-dimensional thermal image to correspond to a two-dimensional (2D) image frame acquired by the image sensor 12. For example, a detected value of each pixel of the 2D thermal image indicates a temperature of a detected region, and the detected regions corresponding to adjacent pixels of the 2D thermal image are arranged to overlap partially or not overlapped with each other depending on the microlens arrangement thereupon.

Compared with the conventional temperature sensor that performs the thermal sensing or temperature sensing by contacting the object to be detected, the thermal sensor 11 of the present disclosure is capable of detecting the temperature by non-contacting with the object to be detected because the thermal sensor 11 can be a thermopile sensor or a bolometer sensor. In other words, the thermal sensor 11 of the present disclosure can detect the temperature of a target (e.g., human body) even though the target is covered by clothes or cloth thereby having higher reliability and applicability.

The image sensor 12 includes, for example, a CCD image sensor, a CMOS image sensor or the like, which has multiple pixels arranged in a matrix to output the 2D image frame.

The processor 13 is, for example, a digital signal processor (DSP), a microcontroller (MCU), a central processing unit (CPU), an application specific integrated circuit (ASIC), a graphic processing unit (GPU) or the like. The processor 13 is electrically coupled to the thermal sensor 11 and the image sensor 12 to respectively receive a thermal image Ih and an image frame Im for the post-processing by software and/or hardware. The processor 13 also controls ON/OFF of the thermal sensor 11 and the image sensor 12 as well as operation of pixels thereof.

The memory 14 includes, for example, a volatile memory and/or non-volatile memory. The memory 14 is used to previously record the algorithm, threshold(s) and parameter(s) used by the processor 13 in the post-processing. In different applications, the memory 14 further temporarily stores data of the thermal image Ih and/or the image frame Im detected during operation.

Figure 2A:
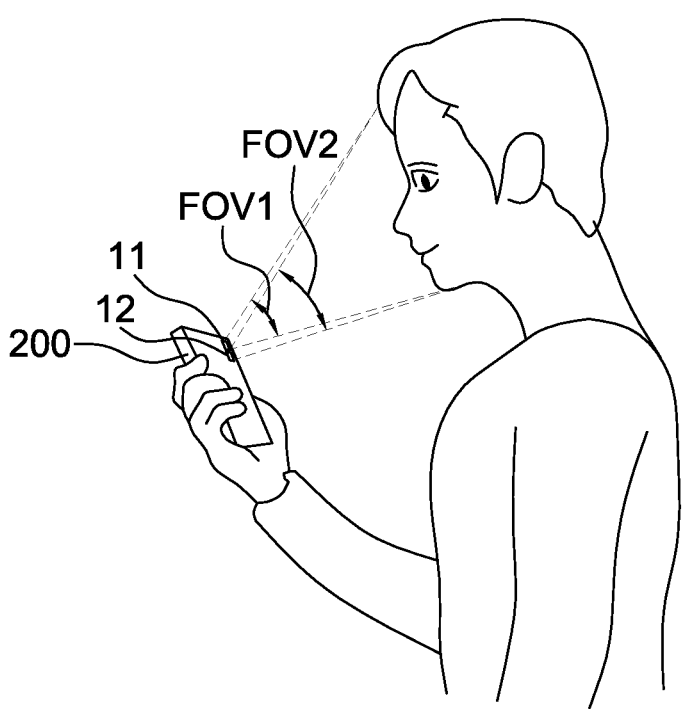
FIG. 2A is an operational schematic diagram of a face recognition system according to a first embodiment of the present disclosure.
Figure 2B:
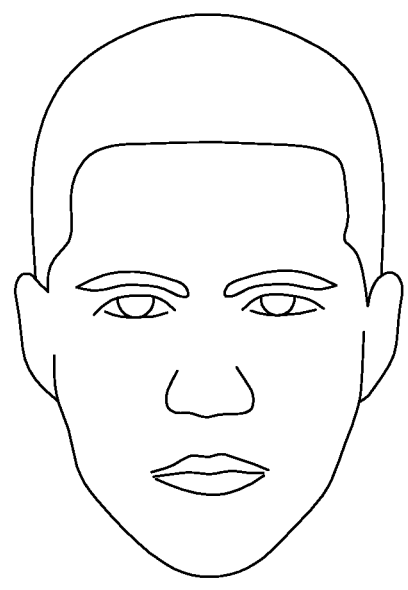
FIG. 2B is a schematic diagram of a face image acquired by a face recognition system according to a first embodiment of the present disclosure.
Figure 2C:
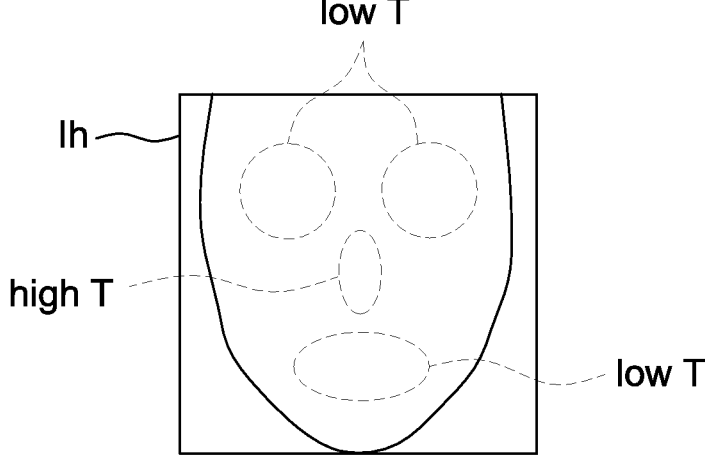
FIG. 2C is a schematic diagram of a temperature distribution of a thermal image acquired by a face recognition system according to a first embodiment of the present disclosure.

Referring to FIG. 2A, it is a schematic diagram of a face recognition system 200 according to a first embodiment of the present disclosure. FIG. 2A shows the face recognition system 200 being arranged close to the side of a portable device facing the user. The face recognition system 200 includes the thermal sensor 11, the image sensor 12, the processor 13 and the memory 14 shown in FIG. 1. The thermal sensor 11 acquires a thermal image Ih (e.g., FIG. 2C showing the temperature distribution thereof) with a first field of view FOV1, and the thermal image Ih is outputted to the processor 13. The image sensor 12 acquires an image frame Im (e.g., FIG. 2B showing a face image therein) with a second field of view FOV2, and the image frame Im is outputted to the processor 13. To acquire corresponding features, at least a part of FOV1 overlaps with FOV2 to acquire information of the same area or surface using different sensors. The thermal sensor 11 and the image sensor 12 are arranged to simultaneously or alternatively acquire images without particular limitations.

The processor 13 performs the face recognition and/or the material recognition according to the image frame Im, wherein the processor 13 uses the conventional face recognition algorithm to recognize facial features of a face image (e.g., as shown in FIG. 2B), and uses the conventional material recognition algorithm to recognize skin material in the image frame Im. The processor 13 performs the living body recognition according to a regional heat distribution in the thermal image Ih corresponding to the facial features of the face image in the image frame Im.

In an image type unlocking system, to prevent an unregistered person from unlocking the system using a photo or video of a registered face, the face recognition system 200 of the first embodiment of the present disclosure distinguishes a fake according to the thermal image Ih captured by the thermal sensor 11 and the skin material of a face in the image frame Im. Accordingly, the living body herein is referred to a real person instead of a photo or video.

For example in one non-limiting aspect, the processor 13 does not turn on the thermal sensor 11 before identifying that a registered face image is contained in the image frame Im or the registered face image has skin material so as to reduce the power consumption, i.e. the processor 13 turning on the thermal sensor 11 only when a registered face image is identified in the image frame Im or the registered face image has skin material, but the present disclosure is not limited thereto.

In another non-limiting aspect, the processor 13 conversely controls the thermal sensor 11 and the image sensor 12. That is, the processor 13 does not turn on the image sensor 12 before an area of an object image in the thermal image Ih is identified to be larger than a threshold. The processor 13 turns on the image sensor 12 to perform the face recognition only when the thermal image Ih contains a valid face image (i.e. object area larger than the threshold). In other aspects, during the unlocking, the thermal sensor 11 and the image sensor 12 are both turned on or activated.

In the first embodiment, a range covered by a first field of view FOV1 of the thermal sensor 11 is preferably larger than a second field of view FOV2 of the image sensor 12. In addition, as the living body recognition is performed according to the thermal image Ih, the processor 13 only performs the 2D face recognition according to the image frame Im without performing the three-dimensional (3D) face recognition to reduce the power computation. Traditionally, the 3D face recognition can be used to distinguish a photo from a person, but higher calculation loading is required.

In addition, to further prevent an unregistered person to perform the unlocking using a heated photo, the processor 13 not only confirms whether an object image in the thermal image Ih has a temperature larger than a predetermined temperature, but also identifies a regional heat distribution in the thermal image Ih. For example referring to FIG. 2C, the thermal image Ih contains high and low temperature regions, e.g., a high temperature region corresponding to a nose area of the face image (as shown in FIG. 2B) in the image frame Im, and low temperature regions corresponding to eyes and mouth areas of the face image in the image frame Im.

In this case, the memory 14 previously records the temperature distribution of various face regions, which is stored in the memory 14 by detecting a registered user in a setting mode (e.g., entered by executing an application or pressing a key), or obtained by a statistical result which is stored in the memory 14 before shipment. The processor 13 compares (e.g., calculating similarity or correlation) the regional heat distribution in a current thermal image (e.g., a thermal image Ih acquired during the unlocking) with the pre-stored temperature distribution to perform the living body recognition. In addition, the processor 13 calculates a temperature difference between areas of the high and low temperature regions to confirm that an object currently being detected by the face recognition system 200 is indeed a human body rather than a fake.

In another aspect, the processor 13 compares the regional heat distribution in a current thermal image with locations of facial features (e.g., the eyes, nose and mouth) identified from the captured image frame Im to confirm whether the regional heat distribution matches with the corresponding facial features or not. In this way, it is also possible to distinguish a fake from a real human face without recording the temperature distribution previously in the memory 14.

After the confirmation of a registered face is accomplished through the face recognition, the processor 13 then turns on or activates operating functions of an electronic device that adopts the face recognition system 200, e.g., activating the display screen.

Figure 3A:
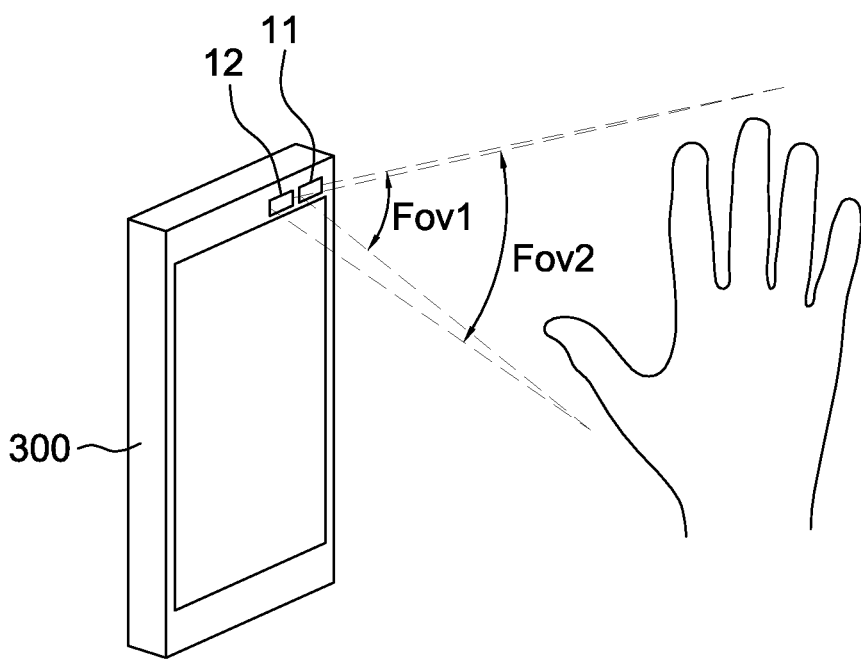
FIG. 3A is an operational schematic diagram of a gesture recognition system according to a second embodiment of the present disclosure.
Figure 3B:
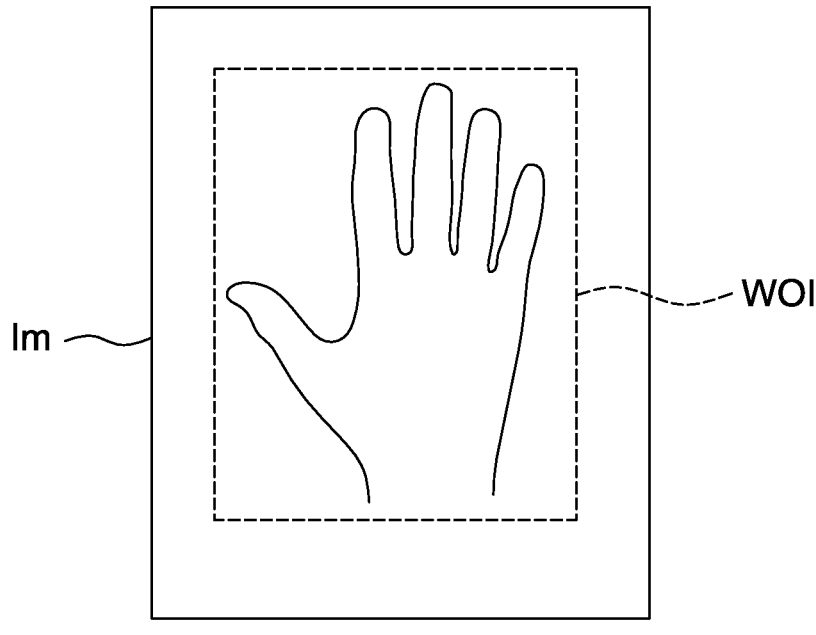
FIG. 3B is a schematic diagram of an image frame acquired by a gesture recognition system according to a second embodiment of the present disclosure.

Referring to FIG. 3A, it is a schematic diagram of a gesture recognition system 300 according to a second embodiment of the present disclosure. FIG. 3A shows the gesture recognition system 300 being arranged at the side of a portable device facing the user. The gesture recognition system 300 also includes the thermal sensor 11, the image sensor 12, the processor 13 and the memory 14 shown in FIG. 1. The thermal sensor 11 is used to acquire a thermal image Ih with a first field of view FOV1, and the thermal image Ih is outputted to the processor 13. The image sensor 12 is used to acquire an image frame Im (as shown in FIG. 3B) with a second field of view FOV2, and the image frame Im is also outputted to the processor 13.

The processor 13 determines a processed region WOI in the thermal image Ih, and performs the gesture recognition according to an image region in the image frame Im corresponding to the processed region WOI determined in the thermal image Ih so as to eliminate the interference from ambient light. Accordingly, to allow the processor 13 to be able to correctly determine the processed region WOI in the image frame Im, in the second embodiment the first field of view FOV1 of the thermal sensor 11 is preferable equal to the second field of view FOV2 of the image sensor 12, and sizes of the thermal image Ih and the image frame Im are preferable identical. For example, a corresponding processed region WOI in the image frame Im is obtained according to pixel addresses or pixel locations within the determined processed region WOI in the thermal image Ih.

For example, the processor 13 identifies a region in the thermal image Ih having a temperature larger than a temperature threshold (determined according to body temperature) as the processed region WOI, which is an image region in the thermal image Ih. As the second field of view FOV2 is arranged corresponding to the first field of view FOV1, the processor 13 confirms a corresponding processed region WOI in the image frame Im as shown in FIG. 3B, wherein a size of the corresponding processed region WOI is smaller than that of the image frame Im. It should be mentioned that the processed range WOI is not limited to a rectangle as shown in FIG. 3B but is another suitable shape as long as it covers the object region in the image frame Im. In some scenarios, two processed regions WOI are defined corresponding to two object regions.

In other aspects, the first field of view FOV1 and the second field of view FOV2 are not totally identical to each other and have an angle difference. In this case, the memory 14 previously stores a space conversion algorithm or matrix transformation algorithm between the thermal image Ih and the image frame Im. In this way, after confirming the processed region WOI in the thermal image Ih, the processor 13 confirms a corresponding processed region WOI in the image frame Im according to the stored algorithm.

In another non-limiting aspect, the processor 13 firstly identifies an object image in the image frame Im, which may also contain an image of ambient light. The processor 13 then removes the non-human image based on the thermal image Ih. For example, the object image outside the processed region WOI is not used in the gesture recognition so as to effectively improve the recognition accuracy and eliminate the interference.

More specifically, in the second embodiment, the processor 13 performs the gesture recognition according to a partial image of the image frame Im, and the thermal image Ih is for the denoising function.

In addition, in the low power consumption scenario, the processor 13 turns on the image sensor 12 only after identifying a processed region WOI in the thermal image Ih larger than a predetermined size. In this case, a whole sensor array of the image sensor 12 is turned on or a part of the sensor array corresponding to the WOI is turned on. In other words, when the thermal image Ih does not contain a region having a temperature higher than a predetermined temperature threshold, the processor 13 only turns on the thermal sensor 11 to capture thermal images Ih at a predetermined frequency; or, even though the thermal image Ih contains a region having a temperature higher than the predetermined temperature threshold, the processor 13 still only turns on the thermal sensor 11 to acquire thermal images Ih at a predetermined frequency if the region is smaller than a predetermined size, which is determined according to a hand size within a detectable distance of the system, but the present disclosure is not limited thereto.

In other aspects, during the gesture recognition, the thermal sensor 11 and the image sensor 12 are both turned on or activated. For example, only a part of pixels of the thermal sensor 11 are turned on, and said the part of pixels corresponds to a pixel region of the image sensor 12 detecting an object. More specifically, in the present disclosure sensor arrays of the thermal sensor 11 and the image sensor 12 are not necessary to be fully turned on but only a part of pixels thereof are turned on to reduce the power consumption.

In an alternative embodiment, the processor 13 performs a material recognition in the image frame Im captured by the image sensor 11 at first and then performs the gesture recognition according to the thermal image Ih captured by the thermal sensor 11. For example, if an object image in the image frame Im is not identified to have skin material by the processor 13, the thermal sensor 11 is not turned on. The thermal sensor 11 is turned on only when a skin material is identified in the image frame Im. Furthermore, the processor 13 also determines a WOI in the thermal image Ih based on a skin material region in the image frame Im, i.e., the processor 13 firstly determining a skin material region in the image frame Im at first and then determining a WOI in the thermal image Ih corresponding to the skin material region. The gesture recognition is performed using the object image only within the WOI in the thermal image Ih.

It should be mentioned that although in the above first and second embodiments the recognition system 100 is illustrated by applying to a portable device, the present disclosure is not limited thereto. The recognition system 100 of the first and second embodiments is also applicable to a wearable device, the security system and/or control system of a gate or a vehicle. The processor 13 performs the living body recognition and denoising using the thermal image Ih to improve the identification accuracy and security.

Figure 4:
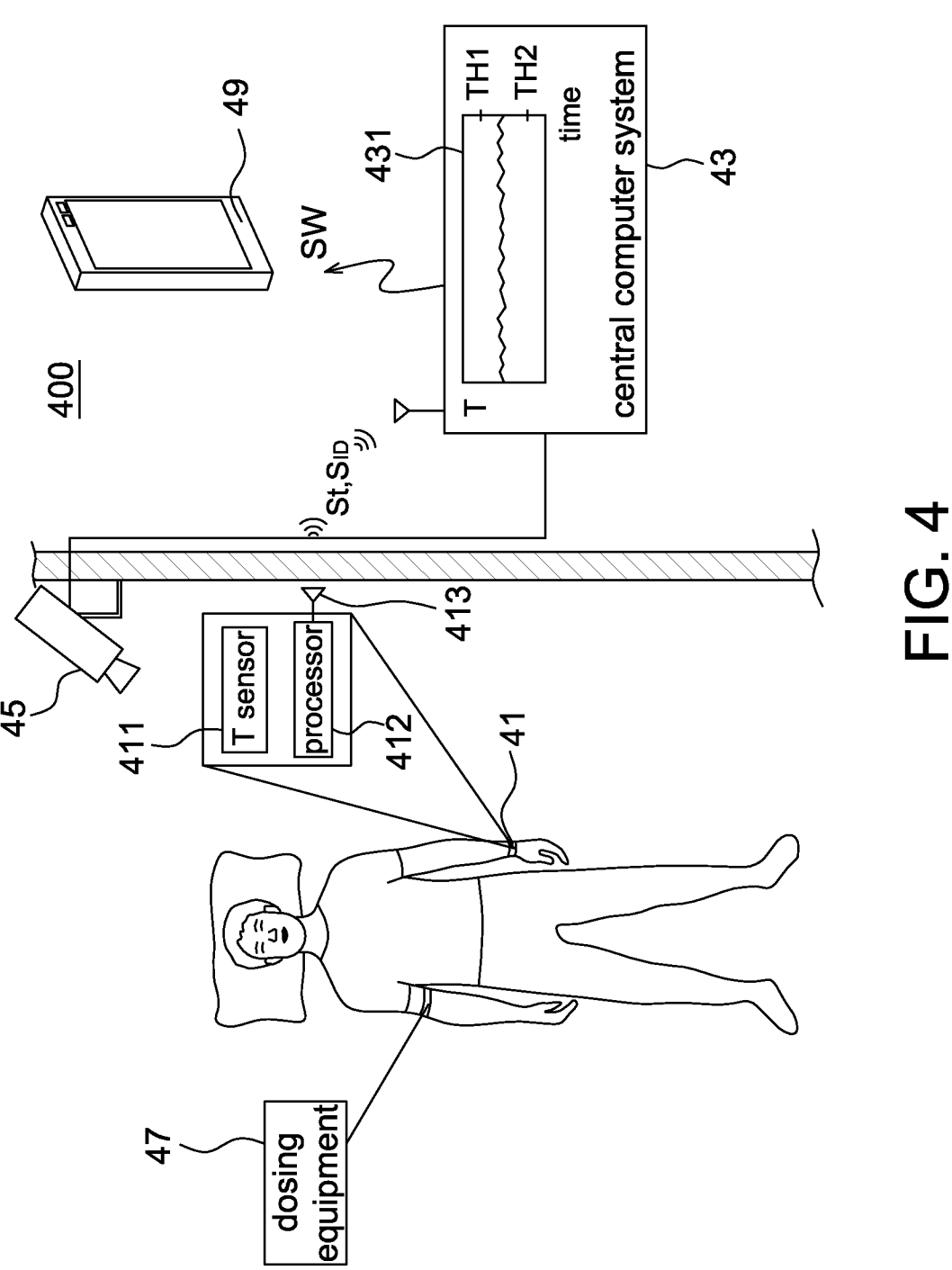
FIG. 4 is a schematic diagram of a medical monitoring system according to a third embodiment of the present disclosure.

Please referring to FIG. 4, it is a schematic diagram of a medical monitoring system 400 according to a third embodiment of the prevent disclosure. The medical monitoring system 400 is applied to a medical institute or a care institute so as to solve the problem caused by the manpower shortage. The medical monitoring system 400 mainly includes a wearable accessory 41 and a central computer system 43 coupled to each other. The wearable accessory 41 is worn on a human body, e.g., FIG. 4 showing on a human arm, but not limited thereto. The wearable accessory 41 is worn on any body part suitable for measuring the body temperature. The central computer system 43 performs a corresponding response, e.g., providing a warning, according to detected results of the wearable accessory 41.

For example, the wearable accessory 41 is a customized accessory, a smart watch, a smart armband, a smart bracelet or the like. The wearable accessory 41 at least includes a thermal sensor (shown as T sensor) 411, a processor 412 and a transmitter 413. The thermal sensor 411 is similar to that in the first and second embodiments for outputting a 2D thermal image, and the processor 412 calculates an average temperature of the 2D thermal image. Besides, in the third embodiment, the thermal sensor 411 includes one sensing unit (e.g., photodiode) and outputs one electrical signal or digital signal at a time to indicate a detected temperature instead of outputting a 2D thermal image. The processor 412 is also a DSP, MCU, CPU, ASIC, GPU or the like.

In the case that the thermal sensor 411 is embedded in other electronic devices not directly contact a user (e.g., the electronic device arranged at the wall or ceiling), the thermal sensor 411 monitors temperature of the whole body of the user. The electronic device provides a warning message St if a temperature difference between the core temperature and limb temperature is larger than a predetermined threshold.

In measuring body temperature, the thermal sensor 411 directly detects a temperature of a skin surface as the body temperature, or detects a temperature difference between the room temperature and the body temperature (i.e. the room temperature and the body temperature being detected simultaneously using identical or different sensors) and obtains the body temperature by subtracting (using the processor 412) the temperature difference from the room temperature.

The thermal sensor 411 is used to detect a body temperature and output an electrical signal or a digital signal to the processor 412. The processor 412 identifies a temperature according to the received signal, and then controls the transmitter 413 (shown by an antenna in FIG. 4) to send a temperature message St associated with the body temperature and a label message $S_{ID}$ of the wearable accessory 41 (e.g., the medical monitoring system 400 including multiple wearable accessories 41 each having an individual label) in a wireless manner such as the Bluetooth communication, Zigbee, microwave communication, but not limited to.

In one aspect, the central computer system 43 is arranged at a suitable location capable of receiving the temperature message St and the label message $S_{ID}$, and used to store the received temperature message St onto cloud or in a memory therein. In another aspect, the central computer system 43 includes multiple receivers arranged at different locations to receive the temperature message St and the label message $S_{ID}$ from different patients, and a host of the central computer system 43 is electrically connected to these receivers.

When the received temperature message St indicates that the body temperature exceeds a predetermined range, the central computer system 43 generates a warning message Sw associated with the label message $S_{ID}$, wherein said associated with the label message $S_{ID}$ is referred to that the warning message Sw is dedicated to a human body who wears the wearable accessory 41 that sends the label message $S_{ID}$ so as to avoid the confusion between patients. In one aspect, the warning message Sw is represented by a lamp or a broadcast. In another aspect, the central computer system 43 further includes a transmitter (not shown) for wirelessly sending the warning message Sw to a portable device 49, which is carried by or assigned to a medical staff.

In one non-limiting aspect, the central computer system 43 further includes a display 431 (e.g., LCD or plasma) for showing a temperature distribution with time of the body temperature to be watched by the medical staff. The display 431 shows or is marked a high temperature threshold TH1 and a low temperature TH2 on the screen thereof. When identifying that the body temperature detected by the thermal sensor 411 exceeds a predetermined range (e.g., higher than TH1 or lower than TH2), the central computer system 43 generates the warning message Sw. The thresholds TH1 and TH2 may be set or adjusted corresponding to different users.

In one non-limiting aspect, the central computer system 43 further includes a camera 45. When identifying that the body temperature exceeds the predetermined range, the central computer system 43 turns on the camera 45 to perform the patient monitoring. In normal time, the camera 45 is turned off to protect the privacy of the patient. Furthermore, images acquired by the camera 45 are selected to be shown on the display 431.

In one non-limiting aspect, the central computer system 43 further includes a dosing equipment 47. When identifying that the body temperature exceeds the predetermined range, the central computer system 43 turns on the dosing equipment to perform the automatic dosing. The operating status of the dosing equipment 47 is selected to be shown on the display 431 if it is included. The display 431 further shows the relationship between the dosage and the variation of body temperature. The central computer system 43 further controls the dosing equipment 47 to stop dosing when the body temperature recovers to be within the predetermined range.

Although in the above embodiment the medical monitoring system 400 is applied to an operation organization, the present disclosure is not limited thereto. The medical monitoring system 400 of the third embodiment is also applicable to a home caring system, and the operation of the central computer system 43 is replaced by a tablet computer, a desktop computer or a notebook computer.

Although the third embodiment is described using a wearable accessory 41, it is only intended to illustrate but not to limit the present disclosure. In other aspects, the wearable accessory 41 is replaced by a monitoring device that is not directly attached to a human body. The thermal sensor 411 detects the body temperature by non-contacting the human body.

Figure 5:
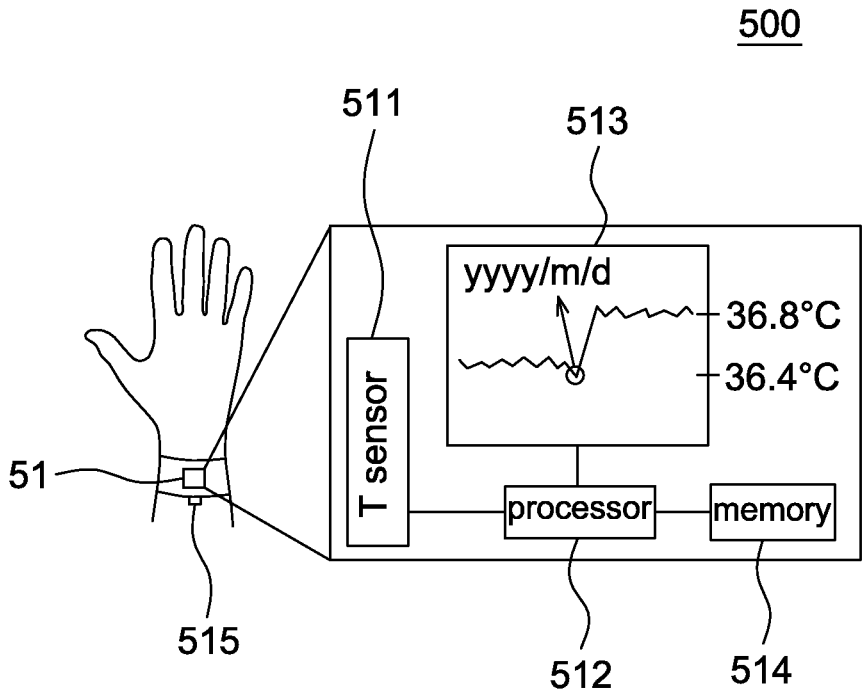
FIG. 5 is a schematic diagram of a body temperature monitoring device according to a fourth embodiment of the present disclosure.

Referring to FIG. 5, it is a schematic diagram of a body temperature monitoring device 500 according to a fourth embodiment of the present disclosure. The body temperature monitoring device 500 includes a wearable accessory 51, a thermal sensor (shown as T sensor) 511, a processor 512, a display 513 and a memory 514. The processor 512 is also a DSP, MCU, CPU, ASIC, GPU or the like.

The wearable accessory 51 is worn on a human body. For example, the wearable accessory 51 is a watch, a bracelet or an armband without particular limitations as long as it is a device attached to and fixed on a skin surface. The thermal sensor 511 is disposed in the wearable accessory 51 and used to detect a basal body temperature (BBT) of a human body, and output an electrical signal or a digital signal to the processor 512. The processor 512 is used to record the BBT every day, and controls the display 513 to give a hint when a temperature variation of the BBT exceeds a temperature variation threshold (e.g., 0.3 to 0.5 degrees which is previously stored in the memory 514).

For example, the processor 512 controls the thermal sensor 511 to measure the BBT at a fixed time of a day every day, e.g., based on a system clock. Or, the body temperature monitoring device 500 further includes a button 515, and when receiving a pressed signal of the button 515, the processor 512 controls the thermal sensor 511 to measure the BBT to be shown on the display 513 and stored in the memory 514 for the long term monitoring.

The display 513 gives various messages using a diagram or numbers, e.g., showing the message including an ovulatory phase or date (e.g., shown by yyyy/m/d), a high temperature interval (e.g., FIG. 5 showing days of BBT at about 36.8 degrees, which is determined according to different users) and a low temperature interval (e.g., FIG. 5 showing days of BBT at about 36.4 degrees, which is determined according to different users) to help the user to know her menstrual period.

Preferably, the BBT is measured when a user wakes up but does not leave the bed yet. Accordingly, to achieve the automatic measurement, the body temperature monitoring device 500 further includes an acceleration detection device (e.g., G-sensor) for detecting whether a user gets out of bed. For example, the acceleration detection device only detects accelerations in two dimensions (e.g., XY axes) before the user gets up, and further detects an acceleration in a third dimension (e.g., Z-axis acceleration) after the user gets up. The processor 512 is further used to identify a wake up time (not leaving bed yet) according to the detected acceleration value of the acceleration detection device, and controls the thermal sensor 511 to automatically detect the BBT at the wake up time. Herein, said detecting an acceleration is referred to that an acceleration value larger than a predetermined threshold is detected.

In one non-limiting aspect, when detecting a user is lying on a bed (e.g., not detecting Z-axis acceleration or other acceleration within a predetermined time interval), the processor 512 controls the thermal sensor 511 to measure a temperature once every a predetermined interval (e.g., one to several minutes). Only the detected temperature before a Z-axis acceleration being detected is taken as the BBT by the processor 512 and stored in the memory 514. To improve the detecting accuracy, if the processor 512 does not detects another Z-axis acceleration within a predetermined time interval after one Z-axis acceleration has been detected, it means that the user only changes a lying posture on the bed and thus the measured temperature temporarily being stored is not considered as the BBT.

In one non-limiting aspect, the temperature monitoring device 500 is further wirelessly coupled to another thermal sensor that includes a wireless transceiver and a processor (e.g., DSP). Said another thermal sensor is arranged near the user or bed. When the temperature monitoring device 500 detects a Z-axis acceleration, a request signal is sent to said another thermal sensor, and the processor of said another thermal sensor recognizes (using hardware and/or software therein to identify a variation of high temperature region in the acquired data) whether the user gets up. If the user gets up, said another thermal sensor sends a response signal to the temperature monitoring device 500 to cause the temperature monitoring device 500 to use a body temperature measured before leaving the bed as the BBT. If the user does not get up, said another thermal sensor does not send a response signal or sends a response signal indicating that it is not necessary to measure a body temperature.

In one non-limiting aspect, when detecting a user shaking the temperature monitoring device 500 in a predetermined pattern (e.g., up-down shaking or left-right shaking for several times), the processor 512 starts to measure a body temperature and records the measured temperature as the BBT.

It is appreciated that numbers mentioned in the above embodiments are only intended to illustrate but not to limit the present disclosure.

It should be mentioned that although the recognition system 100 mentioned above is illustrated to include both the thermal sensor 11 and the image sensor 12, the present disclosure is not limited thereto. In other embodiments, the recognition system 100 includes one of the thermal sensor 11 and the image sensor 12, and receives another signal (e.g., image frame Im or thermal image Ih) from an external sensor via an I/O interface thereof. For example, the recognition system 100 includes the thermal sensor 11 but receives the image frame Im from an external image sensor; or the recognition system 100 includes the image sensor 12 but receives the thermal image Ih from an external thermal sensor.

Figure 6:
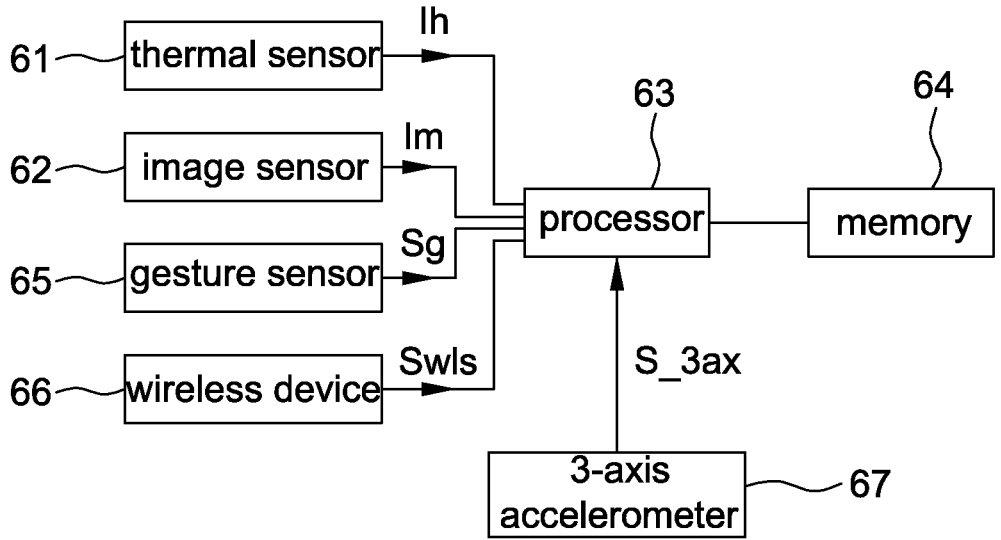
FIG. 6 is a schematic block diagram of an electronic device according to another embodiment of the present disclosure.

Please refer to FIG. 6, it is a schematic block diagram of an electronic device 600 according to another embodiment of the present disclosure. The electronic device 600 is a device controlled by gesture control and employing a digital electronic lock such as an electronic door lock, a vehicle door lock, an electronic safe deposit box or a personal electronic product, but not limited to.

The electronic device 600 includes a thermal sensor 61, an image sensor 62, a processor 62 and a memory 64, which are respectively identical to the thermal sensor 11, the image sensor 12, the processor 13 and the memory 14 mentioned above and thus details thereof are not repeated herein.

The processor 63 performs the unlocking identification and gesture recognition according to an image frame Im captured by the image sensor 62. In the present disclosure, the processor 63 performs the gesture recognition further according to, for example, millimeter wave and time-of-flight. In this case, the electronic device 600 further includes a gesture sensor 65 for outputting a gesture detection signal Sg.

In one aspect, when the processor 63 performs the gesture recognition according to the image frame Im acquired by the image sensor 62, the gesture sensor 65 is the image sensor 62 and the gesture detection signal Sg is the image frame Im.

In another aspect, when the processor 63 performs the gesture recognition according to millimeter wave, the gesture sensor 65 is a millimeter wave radar and the gesture detection signal Sg is output signals of the millimeter wave radar.

In a further aspect, when the processor 63 performs the gesture recognition according to time-of-flight, the gesture sensor 65 is a time-of-flight sensor (e.g., including an SPAD array) and the gesture detection signal Sg is output signals of the time-of-flight sensor, e.g., counting values of pulses.

The methods of identifying a gesture according to the millimeter wave and the time-of-flight are known to the art, and thus details thereof are not described herein.

Figure 7:
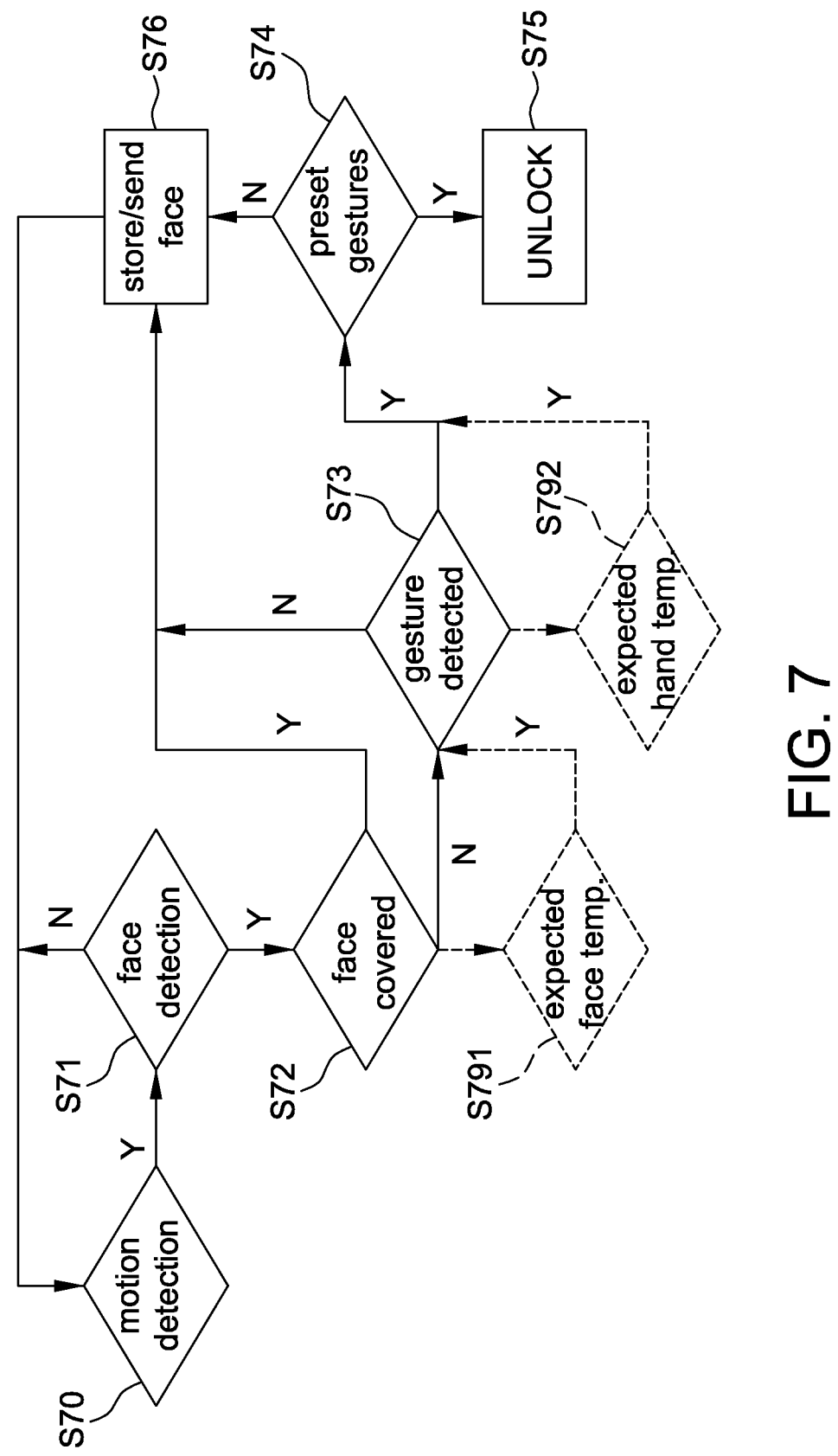
FIG. 7 is a flow chart of an unlocking method of an electronic device according to another embodiment of the present disclosure.

Please refer to FIG. 7, it is a flow chart of an unlocking method of an electronic device 600 according to another embodiment of the present disclosure, including the steps of: detecting motion (Step S70); detecting human face (Step S71); detecting coverage of human face (Step S72); detecting gesture (Step S73) and matching predetermined gesture combination or not (Step S74); if matched, unlocking electronic device (Step S75); if not matching, storing/sending human face image (Step S76). It is appreciated that to execute the present unlocking method, the processor 63 is embedded with a human face recognition algorithm and a gesture recognition algorithm (e.g., implemented by software, firmware and/or hardware), which are known to the art and thus details thereof are not described herein. In one aspect, the human face recognition algorithm only needs to recognize a human face but is not required to recognize identify of the human face.

Step S70: To save power, the processor 63 does not run the human face recognition algorithm or the gesture recognition algorithm before a motion is detected by the image sensor 62. In one aspect, the processor 63 identifies a motion according to image frames Im sequentially outputted by the image sensor 62. In another aspect, a pixel circuit of the image sensor 62 directly detects a motion. The method of detecting a motion using a pixel circuit may be referred to U.S. patent application Ser. No. 17/009,417, entitled "PIXEL CIRCUIT OUTPUTTING PULSE WIDTH SIGNALS AND PERFORMING ANALOG OPERATION" filed on Sep. 1, 2020, assigned to the same assignee of the present application, and the full disclosure of which is incorporated herein by reference.

When a motion is detected, the Step S71 is entered.

For example, the image sensor 62 acquires image frames Im using a first frame rate before a motion is detected, and the image sensor 62 acquires image frames Im using a second frame rate, higher than the first frame rate, after a motion is detected.

Step S71: Next, the processor 63 recognizes (using the human face recognition algorithm) a human face image according to the image frame Im outputted by the image sensor 62. After the image frame Im is recognized with a human face image therein, the Step S72 is entered. However, if no human face image is detected, the Step S70 is returned.

Step S72: In the present disclosure, a complete human face image is set as an unlocking requirement. Therefore, the processor 63 then identifies whether any part, e.g., eyes, noise or mouth, of the human face image in the image frame Im is covered, e.g., by sunglasses, a mask or the like. When the human face image has coverage, the processor 63 records the human face image for being confirmed by a device owner, e.g., the human face image being stored in the memory 64 or sent to the device owner's portable device, i.e. directly entering the Step S76. Meanwhile, the processor 63 does not recognize a gesture and a gesture combination, i.e. not entering the Steps S73 and S74. When the human face image is not covered, the Step S73 is entered.

Step S73: Next, the processor 63 identifies whether a gesture is detected according to the gesture detection signal Sg of the gesture sensor 65. As mentioned above, the gesture sensor 65 is the image sensor 62 or an additional millimeter wave radar or a time-of-flight sensor without particular limitations. That is, when the image sensor 62 is not used to detect a gesture, the image sensor 62 is only used to detect a motion and to acquire a human face image. If no gesture is detected, the Step S76 is entered to store/send the human face image to be confirmed by the device owner. If a motion is detected, the Step S74 is entered.

Step S74: In the present disclosure, the processor 63 determines whether to unlock the electronic device 600 according to whether a series of gestures, called gesture combination herein, match a predetermined sequence/variation or not. When the gesture combination fulfills a predetermined condition (e.g., including sequence or variation), the Step S75 is entered to unlock the electronic device 600. The functions of the electronic device 600 being locked in a locking state are determined according to different operation systems embedded in the electronic device 600 without particular limitations, but at least the unlocking method in FIG. 7 can be executed.

Figure 8A:
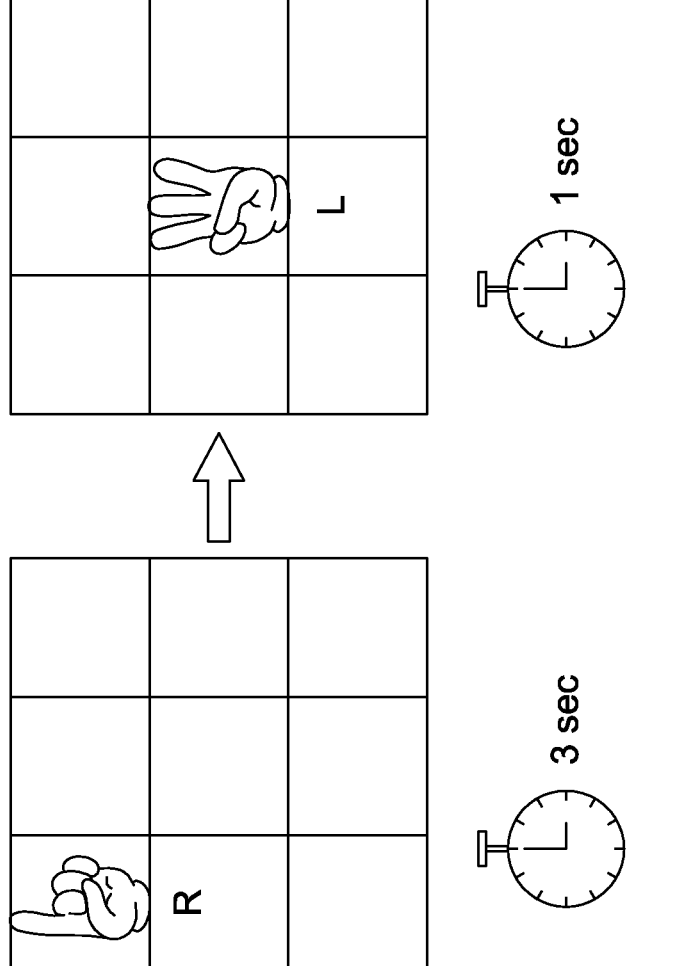
FIGS. 8A to 8F are schematic diagrams of gesture combinations adapted to the unlocking method in FIG. 7.

In one aspect, the gesture combination includes a combination of a static single hand gesture, an operation hand (left hand or right hand), a gesture position and a staying time of gesture. For example, FIG. 8A shows that the gesture combination includes: a right hand (shown as R) of user, with one finger stretching out, staying within a top-left corner pixel region for three seconds within a first time interval; and a left hand (shown as L) of user, with three fingers stretching out, staying within a central pixel region for one second within a second time interval. Lengths of the first time interval and second time interval are preferably determined previously.

Figure 8B:
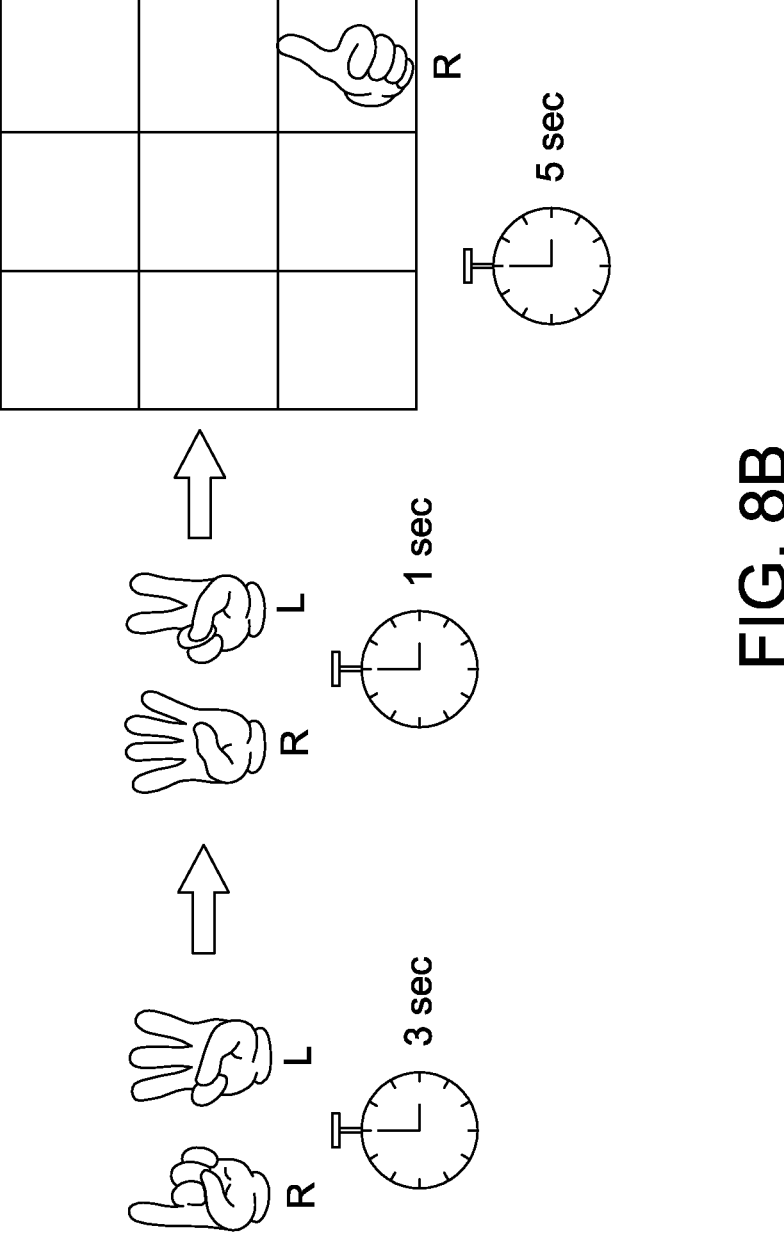

In another aspect, the gesture combination includes a combination of a static two-hand gesture, a static single hand gesture, an operation hand, a gesture position and a staying time of gesture. For example, FIG. 8B shows that the gesture combination includes: a right hand (shown as R), with one finger stretching out, and a left hand (shown as Left), with three fingers stretching out, of user having different gestures staying for three seconds within a first time interval (limiting or not limiting pixel region without particular limitations); the right hand (shown as R), with four fingers stretching out, and the left hand (shown as Left), with two fingers stretching out, of user having changed gestures staying for one second within a second time interval (limiting or not limiting pixel region without particular limitations); and the right hand (shown as R), with thumb stretching out, of user staying within a lower-right corner pixel region for five seconds within a third time interval. Lengths of the first, second and third time intervals are preferably determined previously.

Figure 8C:
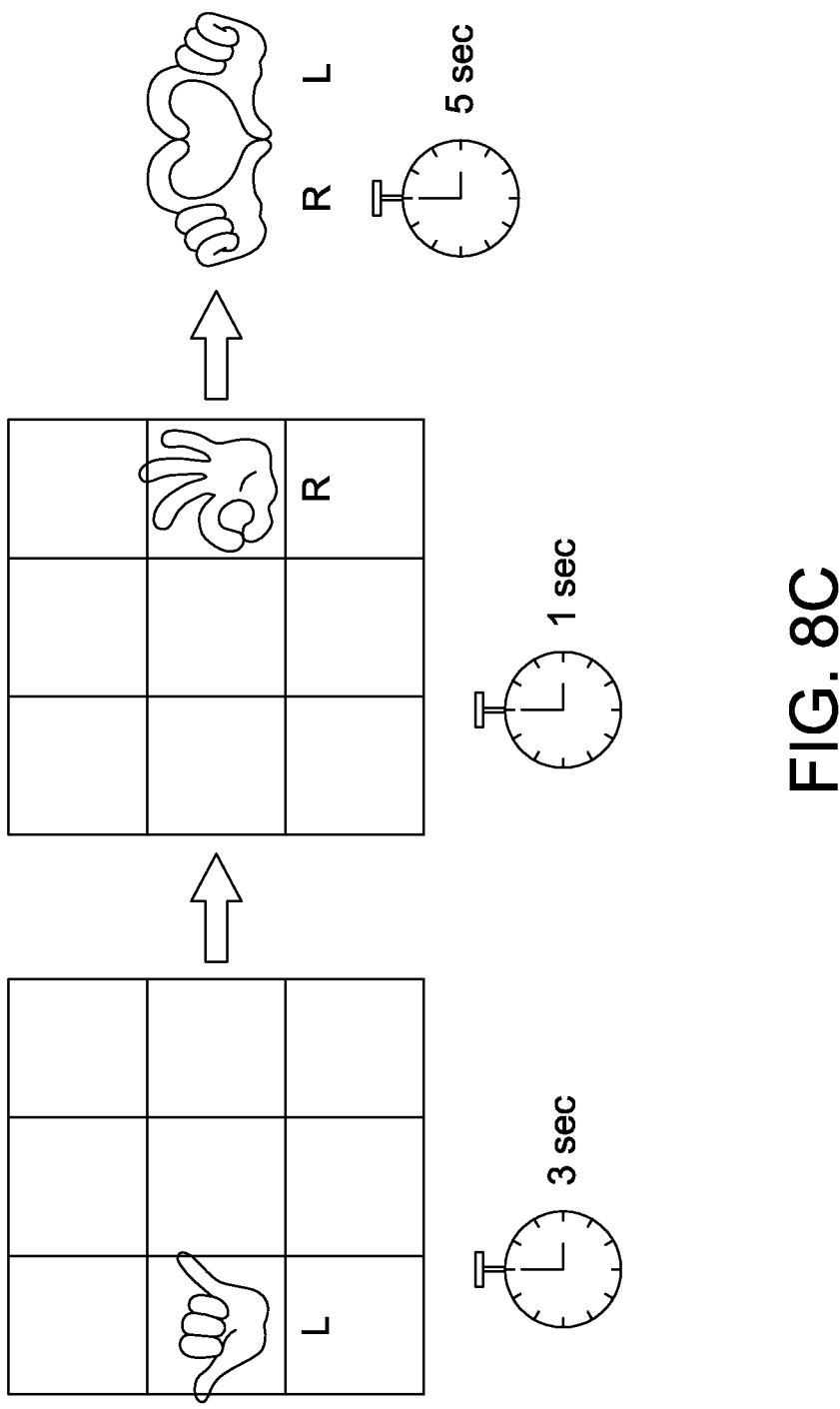

The gestures, positions and times mentioned above are determined before shipment or defined by the device owner. For example, FIG. 8C shows that the gesture combination includes: a left hand (shown as L), with thumb and little finger stretching out, of user staying within a left-center pixel region for three seconds within a first time interval; a right hand (shown as R), indicating OK gesture, of user staying within a right-center pixel region for three seconds within a second time interval; and a combined gesture of the right hand and the left hand, with thumbs touched and little finger touched to form a heart shape, staying for five seconds within a third time interval (limiting or not limiting pixel region without particular limitations).

In this embodiment, a number of pixel regions of a field of view of the image sensor 62 being divided is not limited to nine regions, and the number is determined, e.g., according to a size of field of view and an operation distance.

Figure 8E:
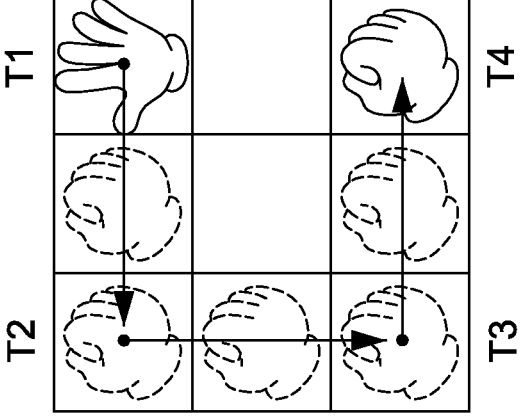
Figure 8D:
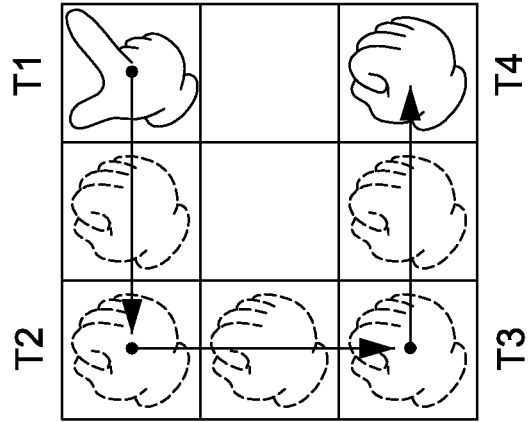

In a further aspect, the gesture combination includes a combination of a dynamic gesture variation, a position variation, a moving direction and a moving speed of a single hand. For example, FIG. 8D and FIG. 8E show that the gesture combination includes: a hand of user (limiting or not limiting operation hand without particular limitations) staying at a top-right corner pixel region with five fingers spread out (e.g., shown in FIG. 8D) or only a part of fingers spread out (e.g., shown in FIG. 8E) within a first time interval T1; the hand of user staying at a top-left corner pixel region to make a fist within a second time interval T2; the hand of user staying at a lower-left corner pixel region to keep the fist within a third time interval T3; and the hand of user staying at a lower-right corner pixel region to keep the fist within a fourth time interval T4; but the sequence is reversible. In addition, the gesture staying time at the pixel region may be involved as mentioned in FIGS. 8A to 8C to form another aspect.

Figure 8F:
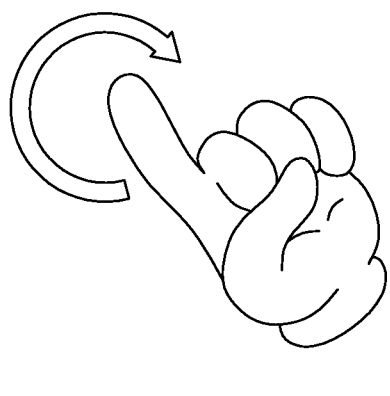
Figure 8F:
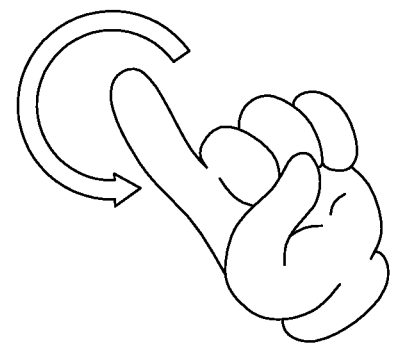

For example, FIG. 8F shows that the gesture combination includes a rotating direction (e.g., clockwise or counter-clockwise), a number of rotations and a rotating speed of a predetermined gesture (e.g., shown as stretching out fore-finger). This aspect is possibly to be arranged to operate with limited or non-limited operation hand without particular limitations.

It is appreciated that the static gesture, dynamic gesture, operation hand, gesture position, and staying time of gesture of the present disclosure are not limited to those mentioned herein.

Meanwhile, in order to let the user know the gesture position and the staying time of gesture, the electronic device 600 of the present disclosure further includes a display or is wirelessly coupled to a display (e.g., the display on a portable device, which is wirelessly coupled to the electronic device 600). The display shows the gesture position and the staying time of gesture thereon.

When recognizing that the gesture combination does not fulfill/match the predetermined condition, the Step S76 is entered to store/send the human face image acquired by the image sensor 62 for the confirmation by device owner.

To further increase the strength of the digital electronic lock, the electronic device 600 of the present disclosure further includes a thermal sensor 61 for outputting a thermal image Ih. The processor 63 further identifies whether a face temperature and a hand temperature satisfies a predetermined temperature, i.e. performing living body recognition.

For example as shown in FIG. 7, in the Step S72, while identifying that the human face image has no coverage, the processor 63 firstly identifies whether a human face has a temperature within a predetermined range (e.g., determined according to previous measurements) according to the thermal image Ih. If the face temperature is not within the predetermined range, the Step S76 is entered;

and the Step S73 is entered only when the face temperature is within the predetermined range. For example in the Step S73, while identifying that a gesture is detected, the processor 63 firstly identifies whether a hand temperature is within a predetermined range (e.g., determined according to previous measurements) according to the thermal image Ih. If the hand temperature is not within the predetermined range, the Step S76 is entered; and the Step S74 is entered only when the hand temperature is within the predetermined range. The method of determining an object temperature according to a thermal image is known to the art, and thus details thereof are not described herein.

Figure 9:
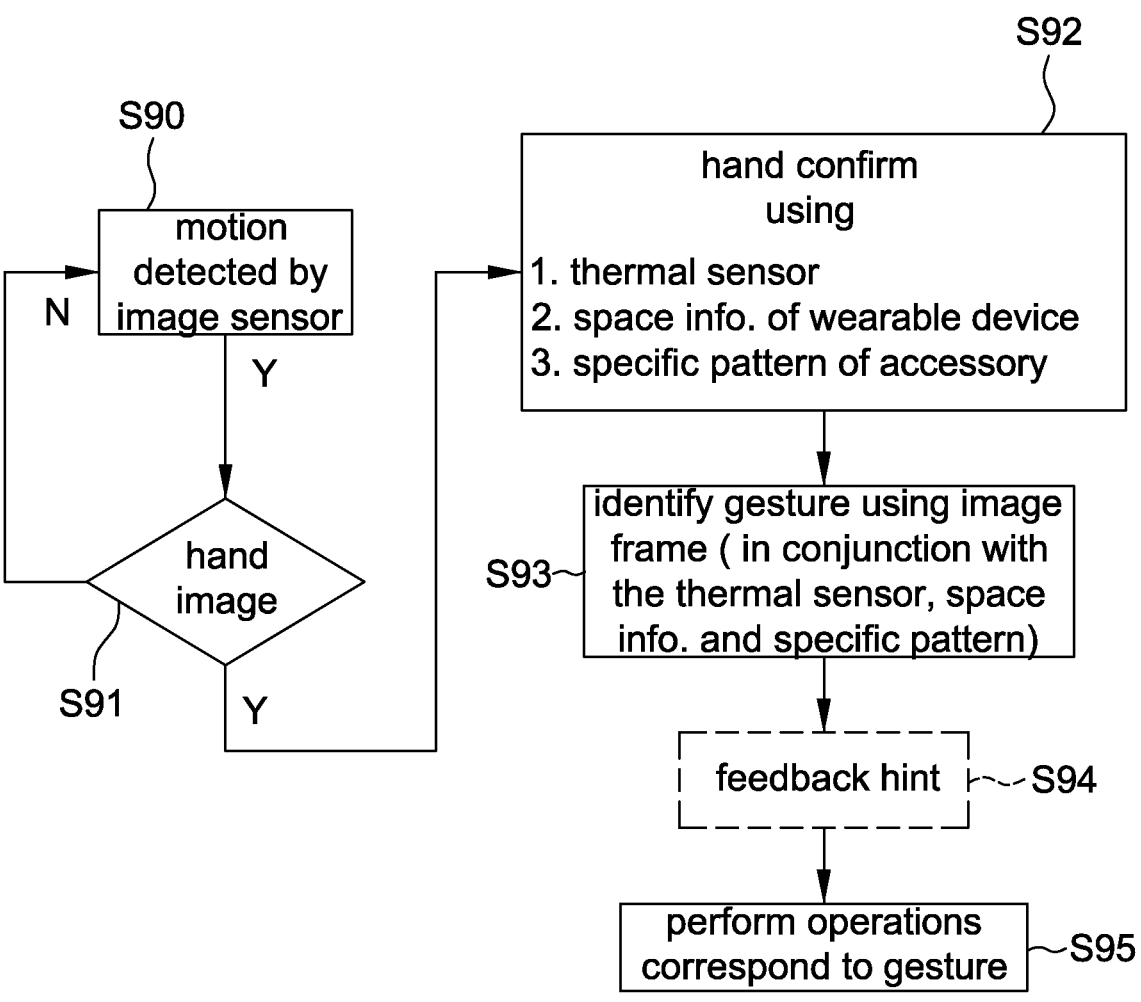
FIG. 9 is a flow chart of a gesture recognition method of an electronic device according to another embodiment of the present disclosure.

Please refer to FIG. 9, it is a flow chart of a gesture recognition method of an electronic device 600 according to another embodiment of the present disclosure, including the steps of: detecting motion (Step S91); detecting hand image (Step S91); confirming user's hand (Step S92); identifying gesture (Step S93); detection hint feedback (Step S94); and executing corresponding operations of gesture (Step S95).

Figure 10A:
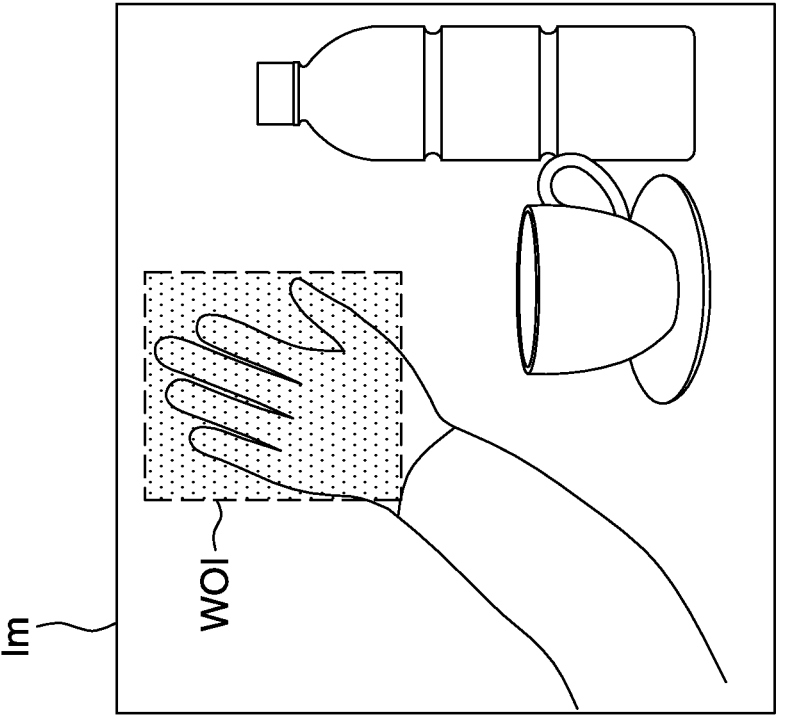
FIGS. 10A to 10C are schematic diagrams of confirming a user hand by a thermal sensor adapted to the gesture recognition method in FIG. 9.

Similarly, the image sensor 62 is used to detect a motion and acquire an image frame Im containing a hand image. As shown in FIG. 10A, in addition to a hand image, the image frame Im further includes other environmental images possibly being recognized by the processor 63. Therefore, the present disclosure further uses a thermal sensor, space information of a wearable device and/or a specific pattern of an accessory to improve the accuracy of gesture recognition and remove environmental interference.

Step S90: To save power, before the image sensor 62 detects a motion, the processor 63 does not execute the gesture recognition algorithm and turns off an illumination light source, e.g., an infrared light source (not shown), but not limited to. The motion detection has been illustrated above, and thus details thereof are not repeated again. When the processor 63 confirms a motion (e.g., calculated according to image frames or according to a calculation result of pixel array as mentioned above), the Step S91 is entered.

Step S91: Since this method is mainly used to perform the gesture control, the processor 63 then identifies whether the image frame Im contains a hand image (e.g., calculated by a hand recognition algorithm, which is implemented by software, firmware and/or hardware). In this step, the processor 63 does not recognize a gesture but only identifies a hand object in the image frame Im. To improve the identification accuracy of the hand object, in this step the processor 63 controls the illumination light source to turn on. If no hand image is detected or captured, the Step S90 is returned; whereas if a hand image is detected/captured, the Step S92 is entered.

Step S92~S93: As mentioned above, because the gesture control is easily influenced by environment, the gesture recognition method of the present disclosure further confirms the window of interest (WOI) in the image frame Im, i.e. confirming hand image, according to at least one of a thermal sensor, a wearable device and an accessory.

Figure 10B:
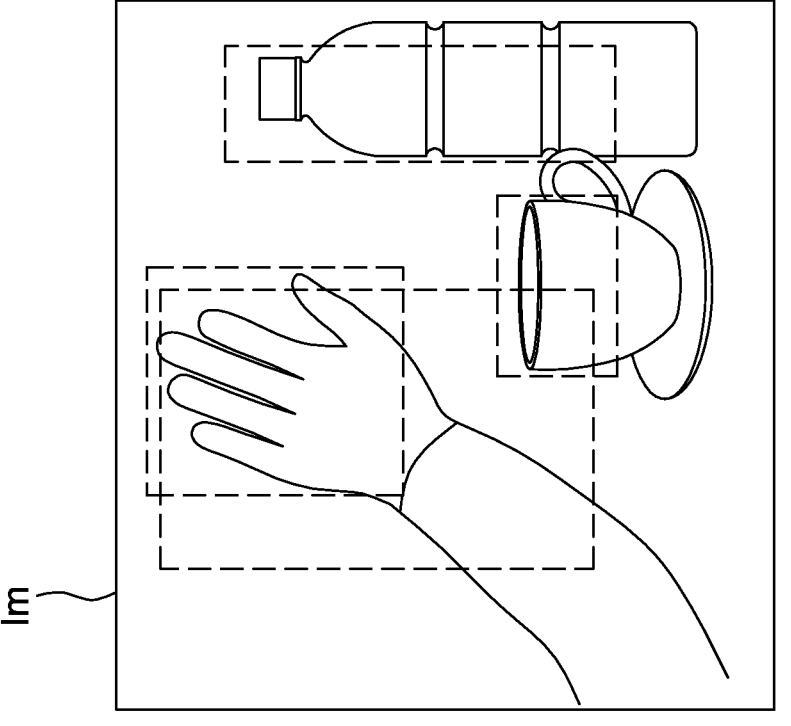

Please referring to FIG. 10B, the processor 63 receives a thermal image Ih from the thermal sensor 61 and determines a processed region in the thermal image Ih and correspondingly determines a WOI in the image frame Im. The method of determining a processed region and a corresponding WOI has been illustrated in FIG. 3B and corresponding descriptions, and thus details thereof are not repeated again.

Figure 10C:
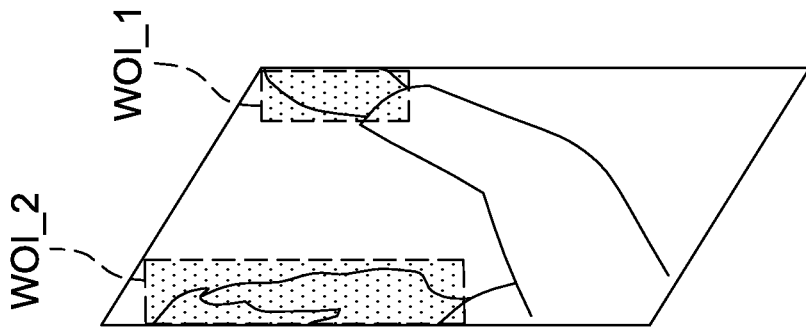
Figure 10C:
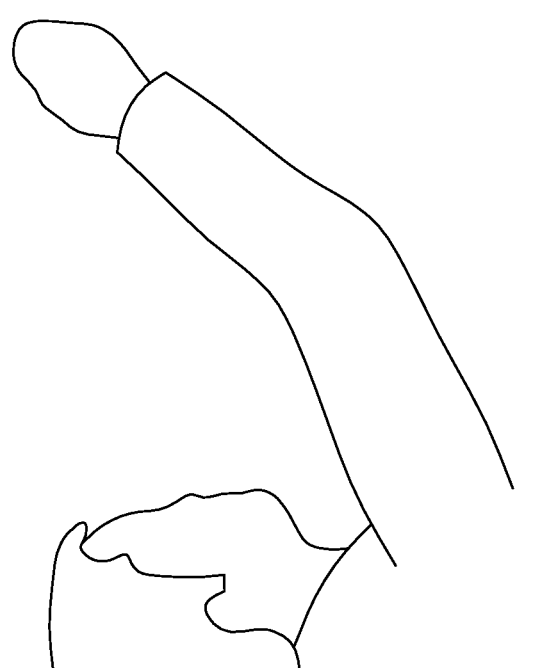

In one aspect, when the processor 63 determines two WOIs according to the thermal image Ih, e.g., FIG. 10C showing a WOI_1 corresponding to a hand and a WOI_2 corresponding to a human face, the processor 63 is arranged to select one of the two WOIs to perform the gesture recognition. Because the user's hand is generally closer to the electronic device 600 in gesture operation, WOI_1 generally indicates a higher temperature, and WOI_2 generally indicates a lower temperature. The processor 63 is arranged to perform the gesture recognition using the WOI in the image frame Im indicating a higher temperature. In addition, the WOI_1 generally has a smaller moving vector, and the WOI_2 generally has a larger moving vector. The processor 63 is further arranged to select one WOI among the two WOIs according to both the temperatures and moving vectors.

Figure 11:
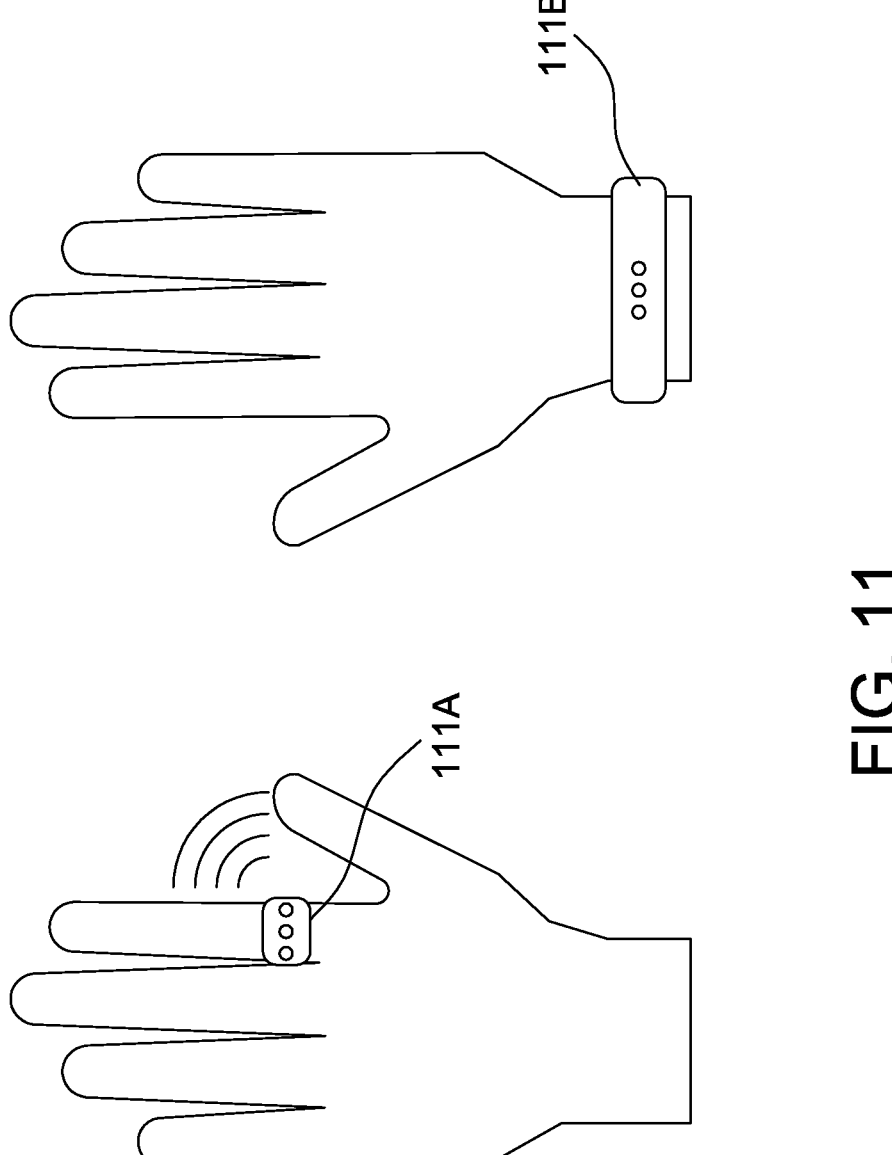
FIG. 11 is a schematic diagram of confirming a user hand by a specific pattern of an accessory adapted to the gesture recognition method in FIG. 9.

Please refer to FIG. 11, the user wears an accessory with a specific pattern on his/her hand during the gesture control. For example, FIG. 11 shows the accessory is a ring 111A on finger, a bracelet or a watch 111B on wrist, but not limited thereto. The specific pattern is a picture or an appearance of the accessory, or a pattern formed by emission light of light sources thereon without particular limitations. Therefore, the processor 63 recognizes the specific pattern according to the image frame Im, and performs the gesture recognition (e.g., using embedded gesture recognition algorithm) according to the hand image and the specific pattern.

Please refer to FIGS. 10C and 11, when the processor 63 determines two WOIs according to the thermal image Ih, e.g., WOI_1 and WOI_2, and because the accessory 111A and/or 111B are worn on the user's hand, the processor 63 is arranged to perform the gesture recognition according to the WOI (e.g., WOI_1 herein) that is closer to the specific pattern in the image frame Im.

Figure 12:
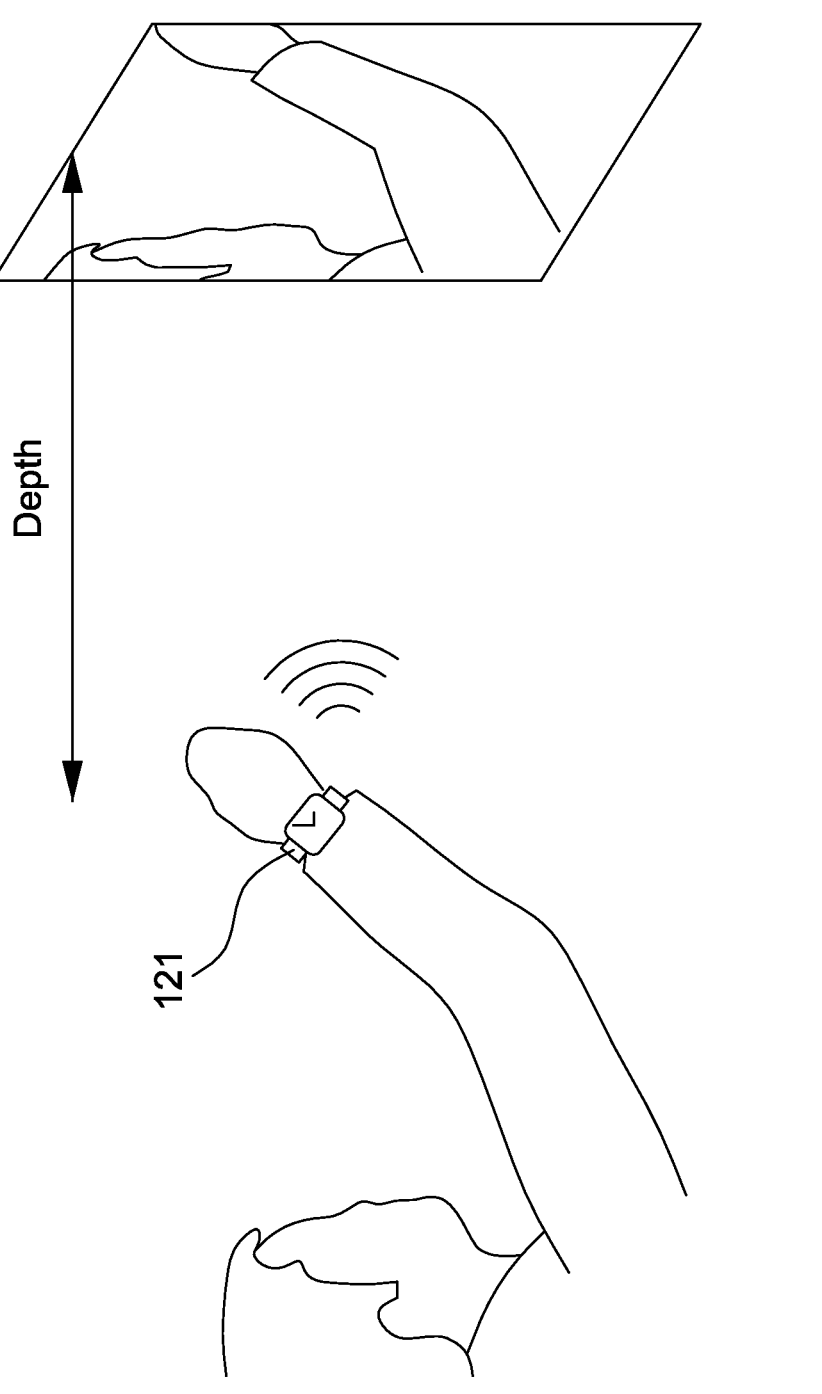
FIG. 12 is a schematic diagram of confirming a user hand by space information of a wearable device adapted to the gesture recognition method in FIG. 9.

Please refer to FIG. 12, the user wears a wearable device 121 capable of transmitting wireless signals during the gesture control, wherein the wearable device 121 is any device that performs the wireless communication, e.g., Bluetooth communication, Wi-Fi communication or RFID, with the electronic device 600 without particular limitations. In this aspect, the electronic device 600 further includes a wireless device 66, e.g., Bluetooth chip, Wi-Fi chip or RFID chip, for the wireless connection. The wireless device 66 receives space information from the wearable device 121.

The processor 63 performs the gesture recognition according to the hand image, the specific pattern and the space information. The space information is, for example, three-dimensional position information (in the case that the processor 63 identifies three-dimensional positions according to wireless signals) or a distance (shown as depth) information (in the case that the processor 63 identifies distances according to strength of wireless signals).

Step S94: In the aspect that the user is wearing the wearable device 121, the processor 63 further informs the wearable device 121 a success message/information via the wireless device 66 after the gesture is recognized. After receiving the success message/information, the wearable device 121 gives a feedback hint. For example, when the wearable device 121 is a watch, a bracelet, a groove or a ring, the feedback hint is set as a vibration; when the wearable device 121 is glasses, contact glasses, virtual reality (VR) equipment, the feedback hint is set as an image or character message; and when the wearable device 121 is an earphone, a neckless, VR equipment, the feedback hint is set as a sound message.

In addition, it is not limited to use the wearable device 121 itself to give the feedback hint, and the feedback hint is given by a device wireless connected to the wearable device 121. For example, the wearable device 121 is wirelessly connected to a vehicle device such as a steering wheel, a central control system, a lookup display and a stereo system of a vehicle. The wearable device 121 sends a signal to the vehicle device to cause the vehicle device to generate a vibration, an image or character message or sound as a hint.

In the present disclosure, the Step S94 is optional, and is involved according to whether the user wears the wearable device 121 and whether the wearable device 121 is wireless coupled to the electronic device 600.

Step S95: Finally, the processor 63 controls the electronic device 600 to execute operations corresponding to the recognized gesture or gesture combination as mentioned above. The operations are determined according to the operation system of the electronic device 600 without particular limitations.

Because the hand confirming mechanism (e.g., Steps S92 to S93) is added, the present disclosure can significantly reduce the environmental interference.

For example, in the aspect that the user wears the accessory 111A or 111B, the processor 63 does not execute the corresponding operations in the Step S95 when identifying that a pixel distance between the hand image and the specific pattern in the image frame Im is larger than a predetermined distance, indicating the hand image not a hand of a current user; or, the processor 63 does not execute the corresponding operations in the Step S95 when identifying that a position relationship between the hand image and the specific pattern is not consistent (e.g., moving directions of the hand image and the specific pattern being different, or sizes of the hand image and the specific pattern indicating different distances), indicating the hand image not a hand of a current user.

For example, in the aspect that the user is wearing the wearable device 121, the processor 63 does not execute operations in the Step S95 when identifying that a position relationship between the hand image and the space information is not consistent. The processor 63 calculates the space information (including three-dimensional positions or depths) according to wireless signals from the wearable device 121 using methods in the art. The present disclosure is to compare whether the position relationship between the space information and the hand image is consistent, e.g., having identical moving direction and similar distances (since wearing on the user's hand) from the electronic device 60 so as to distinguish a current user's hand from environmental interference.

In one aspect, when the accessory 111A or 111B also wirelessly communicates with the electronic device 600 (i.e. sending wireless signals thereto), the processor 63 uses both the specific pattern and the position relationship to identify whether the hand image reflects a current user's hand so as to further improve the gesture accuracy.

The current user mentioned above is referred to a user who is currently controlling the electronic device 600 using the gesture operation.

Figure 13:
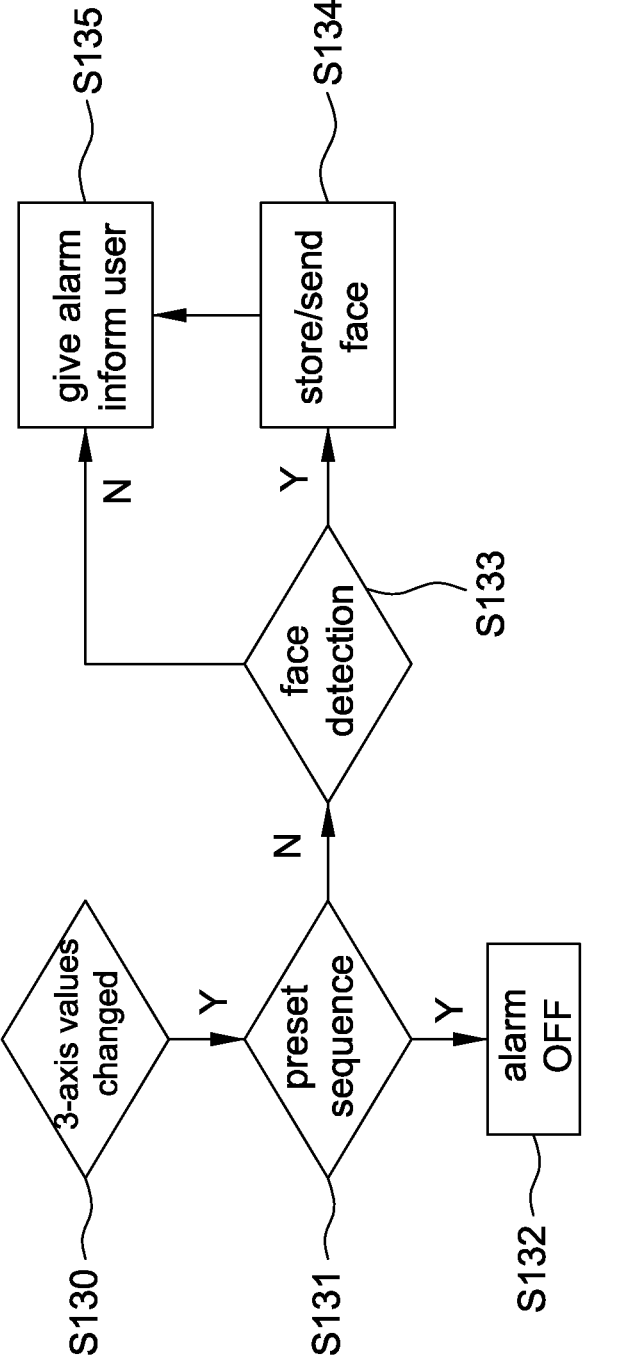
FIG. 13 is a flow chart of a movement alarm method of an electronic device according to another embodiment of the present disclosure.

Please refer to FIG. 13, it is a movement alarm method of an electronic device 600 according to another embodiment of the present disclosure. This method is mainly used to give an alarm and record a human face image for being used later, e.g., informing the owner of the electronic device 600 to know who tried to move the electronic device 600, when the movable electronic device 600 is not moved by a predetermined way.

The movement alarm method of this aspect includes the steps of: detecting three-axis acceleration values (e.g., abbreviated as 3-axis values) (Step S130); whether a variation of the three-axis values matches a predetermined sequence (Step S131); if matched, the Step S132 is entered to turn off the alarm function; but if not matched, giving an alarm and informing user (Step S135). In the aspect that the electronic device 600 further includes an image sensor 62, the movement alarm method further includes the steps of: identifying whether a human face is detected (Step S133) and storing/sending the human face image (Step S134).

Step S130: This embodiment is mainly to arrange a three-axis (shown as 3-axis) accelerometer 67 in the electronic device 600 to output three-axis acceleration values S_3ax, e.g., XYZ axes shown in FIG. 14B. When the processor 63 receives the three-axis acceleration values S_3ax and identifies the acceleration value of at least one axis exceeds a threshold, it means that the electronic device 600 is being moved and thus the Step S131 is entered. That is, if the electronic device 600 is not being moved, an algorithm in the processor 63 for identifying a variation sequence is not run.

Figure 14B:
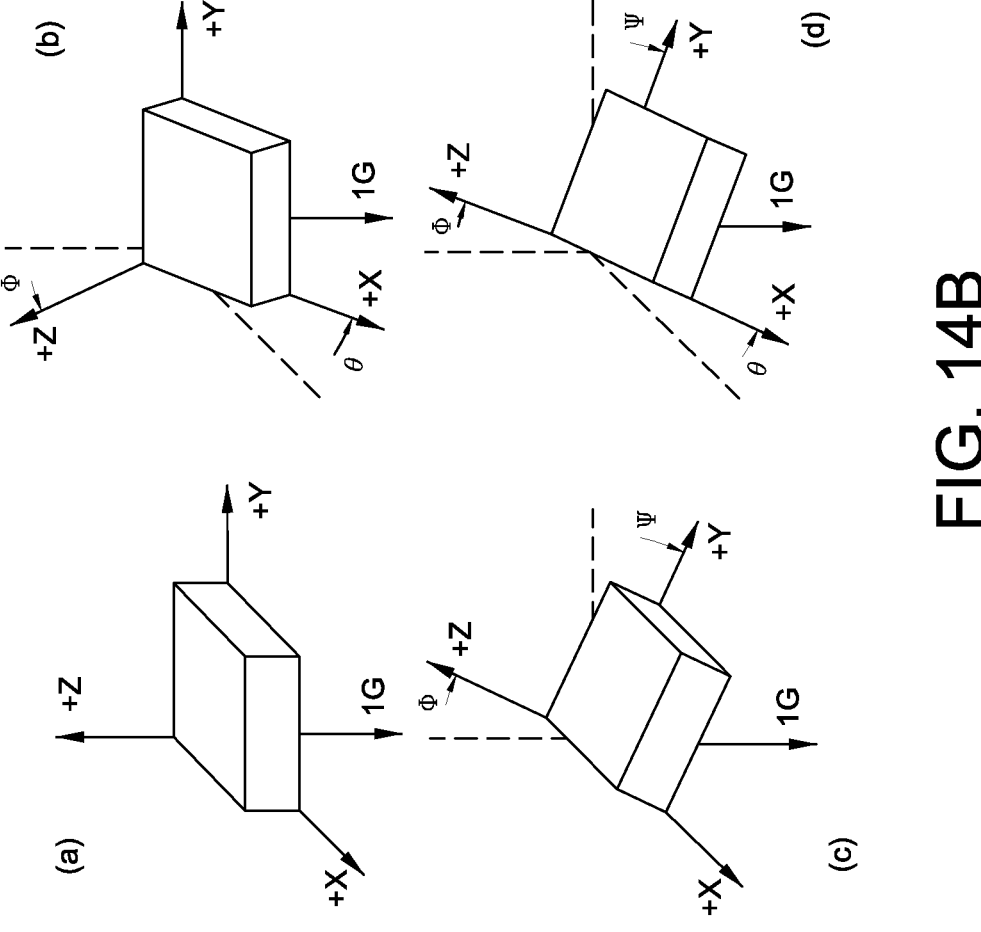
FIG. 14B is a schematic diagram of three-axis values when the electronic device in FIG. 14A is moved.
Figure 14A:
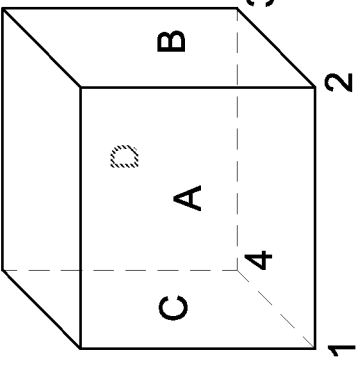
FIG. 14A is a schematic diagram of four surfaces and four corners of an electronic device according to another embodiment of the present disclosure.

Step S131: Because the variation sequence needs to be detected, the processor 63 identifies the three-axis acceleration values S-3ax for at least two time intervals. FIG. 14A shows that the electronic device 600 has four surfaces A to D and four corners 1 to 4. The diagram (a) in FIG. 14B shows a status of three-axis acceleration values when the electronic device 600 is not moved; the diagram (b) in FIG. 14B shows a variation of three-axis acceleration values when the surface D (back surface in FIG. 14B) of the electronic device 600 is lifted up; the diagram (c) in FIG. 14B shows a variation of three-axis acceleration values when the surface C of the electronic device 600 is lifted up;

and the diagram (d) in FIG. 14B shows a variation of three-axis acceleration values when the corner 4 of the electronic device 600 is lifted up. One of ordinary skilled in the art would understand a variation of three-axis acceleration values when other surfaces or corners are lifted up, and thus details thereof are not shown herein. The predetermined sequence is any sequence previously determined, e.g., firstly lifting the surface D, then lifting the surface C and finally lifting the corner 4 as shown in FIG. 14B, but the present disclosure is not limited thereto.

Step S132: When the processor 63 identifies that a variation of three-axis acceleration values S_3ax matches a predetermined sequence, it means that a current user is a valid user and thus the alarm function is closed (i.e. no alarm bine given).

Step S135: When the processor 63 identifies that a variation of three-axis acceleration values S_3ax does not match the predetermined sequence, it means that a current user is not a valid user and thus the alarm is given and the user is informed. The alarm can be given using sound or light without particular limitations. In some systems, the alarm also automatically closes the windows and doors. Said informing user includes sending a message to the user's portable device but not particularly limited as long as the user is informed to know the electronic device 600 is now being moved.

Step S133: In the aspect that the electronic device 600 includes an image sensor 62, the processor 63 further identifies (e.g., using embedded human face recognition algorithm) whether an image frame Im captured by the image sensor 62 includes a human face image. The processor 63 only identifies a human face but is not required to recognize identify of the human face.

Step S134: If a human face image is included, the processor 63 stores the human face image into the memory 64 for being confirmed later, or the human face image is sent to the user's portable device, e.g., cellphone. After the human face image is stored/transmitted, the processor 63 controls the electronic device 600 to give an alarm, i.e. entering the Step S135. If no human face image is contained, the processor 63 controls the electronic device 600 to directly generate an alarm and inform the user, i.e. entering the Step S135. In another aspect, the Steps S134 and S135 are executed simultaneously.

The present embodiment can provide the device owner with the human face image of an invalid user to improve the using security of the device. In this embodiment, the Steps S133 and 134 are optional.

As mentioned above, the recognition system and monitoring system using only the image sensor has its operational limitation such that a complicated algorithm has to be used to overcome this limitation. Accordingly, the present disclosure further provides a face recognition system, (e.g., FIG. 2A), a gesture recognition system (e.g., FIG. 3A), a medical monitoring system (e.g., FIG. 4) and a body temperature monitoring device (e.g., FIG. 5) that overcome the limitation of a system using only the image sensor by employing a temperature sensor to effectively improve the accuracy of a recognition system and broaden the adaptable scenario of a monitoring system.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. An electronic device, comprising:

an image sensor, configured to output an image frame for detecting a human face image;

a gesture sensor, configured to generate a gesture detection signal; and a processor, configured to recognize whether any facial feature of a human face is covered by an object or not according to the human face image, recognize a gesture combination according to the gesture detection signal after no facial feature of the human face is recognized being covered, and unlock a digital electronic lock of the electronic device when the gesture combination is recognized matching a predetermined condition to replace unlocking the digital electronic lock by physiological characteristics, wherein the gesture combination comprises a static two-hand gesture staying for a predetermined seconds to unlock the digital electronic lock.

2. The electronic device as claimed in claim 1, further comprising a thermal sensor configured to output a thermal image, wherein the processor is further configured to identify whether a temperature of the human face and a hand temperature match a predetermined temperature according to the thermal image.

3. The electronic device as claimed in claim 1, wherein the gesture sensor is the image sensor, a millimeter wave radar or a time-of-flight sensor.

4. The electronic device as claimed in claim 1, wherein the processor is further configured not to recognize the gesture combination when the facial feature of the human face is recognized being covered by the object.

5. The electronic device as claimed in claim 1, wherein the processor is further configured to send the human face image to a portable device for being confirmed by a user when the gesture combination is recognized not matching the predetermined condition.

6. The electronic device as claimed in claim 1, wherein the gesture combination further comprises a combination of a static single hand gesture, an operation hand of the static single hand gesture, a gesture position of the static single hand gesture and a staying time of the static single hand gesture, and the electronic device further comprises a display or is wirelessly coupled to a display, and the display is configured to show the gesture position and the staying time of gesture.

7. The electronic device as claimed in claim 1, wherein the gesture combination further comprises a combination of a static single hand gesture, an operation hand of the static single hand gesture, operation hands of the static two-hand gesture, a gesture position of the static single hand gesture, and a staying time of the static single hand gesture, and the electronic device further comprises a display or is wirelessly coupled to a display, and the display is configured to show the gesture position, the gesture positions, the staying times and the staying time of gesture.

8. The electronic device as claimed in claim 1, wherein the gesture combination further comprises a combination of a dynamic gesture variation, a position variation, a moving direction and a moving speed of a single hand.

9. The electronic device as claimed in claim 1, wherein the gesture combination further comprises a predetermined pixel region of the image frame in which the static two-hand gesture staying for the predetermined seconds, and the digital electronic lock is unlocked when the static two-hand gesture stays in the predetermined pixel region for the predetermined seconds.

* * * * *